US012708438B2

(12) United States Patent
Mahmoudi et al.

(10) Patent No.: US 12,708,438 B2
(45) Date of Patent: Aug. 18, 2026

(54) SHUNTING CATHETERS AND METHODS FOR TISSUAL REMOVAL

(71) Applicant: THERAHEART INC., Irvine, CA (US)

(72) Inventors: Rani Abdullah Mahmoudi, Costa Mesa, CA (US); Ajay Kumar Dass, Costa Mesa, CA (US); Wei Gan, Irvine, CA (US)

(73) Assignee: Theraheart Inc., Irvine, CA (US)

( * ) Notice: Subject to any disclaimer, the term of this patent is extended or adjusted under 35 U.S.C. 154(b) by 0 days.

(21) Appl. No.: 18/899,694

(22) Filed: Sep. 27, 2024

(65) Prior Publication Data

US 2026/0090834 A1 Apr. 2, 2026

(51) Int. Cl.

| | |
|---|---|
| ***A61B 18/14*** | (2006.01) |
| *A61B 17/00* | (2006.01) |
| *A61B 17/32* | (2006.01) |
| *A61B 17/3205* | (2006.01) |
| *A61B 18/00* | (2006.01) |

(52) U.S. Cl.

CPC .................... *A61B 18/1492* (2013.01); *A61B 2017/00247* (2013.01); *A61B 2017/320064* (2013.01); *A61B 17/32053* (2013.01); *A61B 2018/00601* (2013.01); *A61B 2217/005* (2013.01)

(58) Field of Classification Search

CPC .......... A61B 18/1492; A61B 17/32053; A61B 2017/00247; A61B 2017/320064; A61B 2018/00601; A61B 2217/005

See application file for complete search history.

(56) References Cited

U.S. PATENT DOCUMENTS

| | | | |
|---|---|---|---|
| 4,861,336 A | 8/1989 | Helzel | |
| 5,255,679 A | 10/1993 | Imran | |
| 5,328,472 A | 7/1994 | Steinke et al. | |
| 5,891,133 A * | 4/1999 | Murphy-Chutorian | A61B 18/24 606/7 |

(Continued)

FOREIGN PATENT DOCUMENTS

| | | |
|---|---|---|
| CA | 2472701 C | 11/2012 |
| CN | 115475001 A | 12/2022 |

(Continued)

OTHER PUBLICATIONS

Babaliaros et al., "Emerging Applications for Transseptal Left Heart Catheterization: Old Techniques for New Procedures," J. Am. Coll.. Cardiol., 2008; 51:2116-22.

(Continued)

*Primary Examiner* — Michael F Peffley
*Assistant Examiner* — Bo Ouyang

(57) ABSTRACT

At least some embodiments of the present disclosure are directed to systems and methods for creating a shunt in a patient. In some embodiments, a shunting catheter includes a catheter shaft including a shaft lumen and a side opening, and a tissue-removal assembly disposed in the shaft lumen in a first state and including a shunting shaft being extendable from the side opening of the catheter shaft. In some examples, the shunting shaft has a curved shape when extending from the side opening to a second state. In some examples, the tissue-removal assembly includes a cutting component disposed at a distal end of the shunting shaft.

31 Claims, 16 Drawing Sheets

(56) References Cited

U.S. PATENT DOCUMENTS

| | | | | |
|---|---|---|---|---|
| 6,179,832 | B1 | 1/2001 | Jones et al. | |
| 6,565,555 | B1 * | 5/2003 | Ryan | A61B 18/24 606/17 |
| 6,726,677 | B1 | 4/2004 | Flaherty et al. | |
| 7,018,400 | B2 | 3/2006 | Lashinski et al. | |
| 7,150,745 | B2 | 12/2006 | Stern et al. | |
| 7,655,005 | B2 | 2/2010 | Bhola | |
| 7,674,256 | B2 | 3/2010 | Marrouche et al. | |
| 7,966,057 | B2 | 6/2011 | Macaulay et al. | |
| 8,043,360 | B2 | 10/2011 | Mcnamara et al. | |
| 8,157,860 | B2 | 4/2012 | Mcnamara et al. | |
| 8,172,896 | B2 | 5/2012 | Mcnamara et al. | |
| 8,214,015 | B2 | 7/2012 | Macaulay et al. | |
| 8,226,619 | B2 | 7/2012 | Miller et al. | |
| 8,252,042 | B2 | 8/2012 | Mcnamara et al. | |
| 8,374,680 | B2 | 2/2013 | Thompson | |
| 8,585,596 | B1 | 11/2013 | Flaherty et al. | |
| 8,617,152 | B2 | 12/2013 | Werneth et al. | |
| 8,728,073 | B2 | 5/2014 | Mcdaniel | |
| 8,758,363 | B2 | 6/2014 | Nishtala et al. | |
| 8,874,237 | B2 | 10/2014 | Schilling | |
| 8,882,697 | B2 | 11/2014 | Celermajer et al. | |
| 8,900,250 | B2 | 12/2014 | Fritscher-Ravens et al. | |
| 8,926,602 | B2 | 1/2015 | Pageard | |
| 8,968,233 | B2 | 3/2015 | Duffy et al. | |
| 9,089,314 | B2 | 7/2015 | Wittenberger | |
| 9,345,858 | B2 | 5/2016 | Flaherty et al. | |
| 9,468,744 | B2 | 10/2016 | Arana et al. | |
| 9,642,993 | B2 | 5/2017 | Mcnamara et al. | |
| 9,789,294 | B2 | 10/2017 | Taft et al. | |
| 9,808,303 | B2 | 11/2017 | Ryba et al. | |
| 9,808,304 | B2 | 11/2017 | Lalonde | |
| 9,814,483 | B2 | 11/2017 | Vardi | |
| 9,918,789 | B2 | 3/2018 | Bagley et al. | |
| 10,016,620 | B2 | 7/2018 | Aljuri et al. | |
| 10,039,905 | B1 | 8/2018 | Taft et al. | |
| 10,154,878 | B2 | 12/2018 | Bloom et al. | |
| 10,188,375 | B2 | 1/2019 | Mcnamara et al. | |
| 10,207,126 | B2 | 2/2019 | Benson | |
| 10,245,352 | B2 | 4/2019 | Wilson et al. | |
| 10,327,791 | B2 | 6/2019 | Morero et al. | |
| 10,426,497 | B2 | 10/2019 | Chou et al. | |
| 10,449,339 | B2 | 10/2019 | Wilson et al. | |
| 10,568,688 | B2 | 2/2020 | Hu et al. | |
| 10,568,751 | B2 | 2/2020 | Mcnamara | |
| 10,624,621 | B2 | 4/2020 | Celermajer | |
| 10,639,060 | B2 | 5/2020 | Vardi et al. | |
| 10,722,300 | B2 | 7/2020 | Gupta et al. | |
| 10,758,714 | B2 | 9/2020 | Laby et al. | |
| 10,842,562 | B2 | 11/2020 | Zhang et al. | |
| 10,857,328 | B2 | 12/2020 | Walzman | |
| 10,864,041 | B2 | 12/2020 | Urbanski et al. | |
| 10,932,723 | B2 | 3/2021 | Eliason et al. | |
| 10,980,552 | B2 | 4/2021 | Mustapha | |
| 10,987,494 | B2 | 4/2021 | Skinner et al. | |
| 10,993,735 | B2 | 5/2021 | Vardi et al. | |
| 10,993,736 | B2 | 5/2021 | Vardi et al. | |
| 11,052,246 | B2 | 7/2021 | Stewart et al. | |
| 11,065,019 | B1 | 7/2021 | Chou et al. | |
| 11,071,585 | B2 | 7/2021 | Zhang et al. | |
| 11,083,520 | B2 | 8/2021 | Ghaly et al. | |
| 11,135,410 | B2 | 10/2021 | Finch et al. | |
| 11,224,449 | B2 | 1/2022 | Chou et al. | |
| 11,224,450 | B2 | 1/2022 | Chou et al. | |
| 11,350,990 | B2 | 6/2022 | Gupta et al. | |
| 11,369,346 | B2 | 6/2022 | De et al. | |
| 11,369,405 | B2 | 6/2022 | Vardi et al. | |
| 11,399,852 | B2 | 8/2022 | Wilson et al. | |
| 11,534,239 | B2 | 12/2022 | Bishara et al. | |
| 11,612,432 | B2 | 3/2023 | Pate et al. | |
| 11,648,042 | B2 | 5/2023 | Kelley | |
| 11,690,609 | B2 | 7/2023 | Celermajer | |
| 11,717,429 | B2 | 8/2023 | Schwartz et al. | |
| 11,752,314 | B2 | 9/2023 | Taft et al. | |
| 11,793,529 | B2 | 10/2023 | Chou et al. | |
| 11,806,032 | B2 | 11/2023 | Chou et al. | |
| 11,865,282 | B2 | 1/2024 | Nae et al. | |
| 11,957,374 | B2 | 4/2024 | Vardi et al. | |
| 12,004,802 | B2 | 6/2024 | Scott et al. | |
| 2002/0111564 | A1 * | 8/2002 | Burbank | A61B 10/0233 606/45 |
| 2005/0154386 | A1 | 7/2005 | West et al. | |
| 2005/0171527 | A1 | 8/2005 | Bhola | |
| 2007/0083194 | A1 | 4/2007 | Kunis et al. | |
| 2008/0009747 | A1 * | 1/2008 | Saadat | A61B 1/04 604/510 |
| 2009/0125097 | A1 | 5/2009 | Bruszewski et al. | |
| 2014/0277045 | A1 | 9/2014 | Fazio et al. | |
| 2014/0277054 | A1 | 9/2014 | Mcnamara et al. | |
| 2016/0175041 | A1 | 6/2016 | Govari et al. | |
| 2018/0236211 | A1 | 8/2018 | Henschel | |
| 2019/0374254 | A1 | 12/2019 | Arevalos et al. | |
| 2020/0030588 | A1 | 1/2020 | Heilman et al. | |
| 2020/0038672 | A1 | 2/2020 | Satake | |
| 2020/0170662 | A1 | 6/2020 | Vardi et al. | |
| 2020/0238059 | A1 | 7/2020 | Wang et al. | |
| 2020/0261704 | A1 | 8/2020 | Wang et al. | |
| 2021/0038298 | A1 | 2/2021 | Scott et al. | |
| 2021/0045805 | A1 | 2/2021 | Govari et al. | |
| 2021/0085384 | A1 | 3/2021 | Maini | |
| 2021/0196373 | A1 | 7/2021 | He et al. | |
| 2021/0315629 | A1 | 10/2021 | Yang et al. | |
| 2021/0369321 | A1 | 12/2021 | Yang et al. | |
| 2021/0393324 | A1 | 12/2021 | Moriyama et al. | |
| 2022/0022954 | A1 | 1/2022 | Shuros et al. | |
| 2022/0110679 | A1 | 4/2022 | Wang et al. | |
| 2022/0202443 | A1 | 6/2022 | Thai et al. | |
| 2022/0249160 | A1 | 8/2022 | Pate et al. | |
| 2022/0257318 | A1 | 8/2022 | Belalcazar | |
| 2022/0265346 | A1 | 8/2022 | Gupta et al. | |
| 2022/0273279 | A1 | 9/2022 | Valdez et al. | |
| 2022/0330975 | A1 | 10/2022 | Rafiee et al. | |
| 2023/0099410 | A1 | 3/2023 | Primeaux | |
| 2023/0210592 | A1 | 7/2023 | Agnew et al. | |
| 2023/0248425 | A1 | 8/2023 | Iijima | |
| 2023/0270491 | A1 | 8/2023 | Mori et al. | |
| 2023/0293877 | A1 | 9/2023 | Hoem | |
| 2024/0050717 | A1 | 2/2024 | Rickerson et al. | |
| 2024/0293147 | A1 | 9/2024 | Mahmoudi | |

FOREIGN PATENT DOCUMENTS

| | | | |
|---|---|---|---|
| EP | 1878453 | B1 | 12/2014 |
| EP | 3238646 | A2 | 11/2017 |
| JP | 5237572 | B2 | 7/2013 |
| WO | 2003/049643 | A1 | 6/2003 |
| WO | 2020/024612 | A1 | 2/2020 |
| WO | 2020/232384 | A1 | 11/2020 |
| WO | 2021/190547 | A1 | 9/2021 |
| WO | 2022/113054 | A1 | 6/2022 |
| WO | 2022/135375 | A1 | 6/2022 |
| WO | 2022/166973 | A1 | 8/2022 |
| WO | 2023/088572 | A1 | 5/2023 |

OTHER PUBLICATIONS

Edwards Lifesciences, "The Alt-Flow II trial for heart failure," 10 pages (undated).

Tanaka et al., "Treatment of Hepatic Encephalopathy Due to Inferior Mesenteric Vein/Inferior Vena Cava and Gonadal Vein Shunt Using Dual Balloon-Occluded Retrograde Transvenous Obliteration," Cardiovasc Intervent Radiol, 2009, 32:390-393 (published online Oct. 7, 2008).

Wilson et al., "Successful Tanscatheter Occlusion of an Anomalous Pulmonary Vein With Dual Drainage to the Left Atrium," Catheter Cardiovasc Interv, 2015, 85:1212-1216 (published online in Wiley Online Library, Apr. 7, 2015).

Patent Cooperative Treaty, International Search Report, mailed Apr. 3, 2025, in PCT/US2024/048908.

(56) References Cited

OTHER PUBLICATIONS

Patent Cooperative Treaty, Written Opinion, mailed Apr. 3, 2025, in PCT/US2024/048908.

* cited by examiner

SHUNTING CATHETERS AND METHODS FOR TISSUAL REMOVAL

FIELD

Certain embodiments of the present disclosure relate to medical systems, apparatus, and methods for creating a shunt in a patient. More specifically, some embodiments of the present disclosure relate to medical systems, apparatus, and methods for creating a shunt on a cardiovascular system wall in a patient.

BACKGROUND

Heart failure is a serious condition that happens when heart cannot pump enough blood and oxygen to support other organs in the body. Heart failure is classified according to left ventricular (LV) function as "heart failure with reduced ejection fraction (EF)" (HFrEF; EF<40%), "mid-range EF" (HFmrEF; EF 40-49%), or "preserved EF" (HFpEF; EF≥50%). About half of patients with heart failure have HFpEF. HFpEF generally happens when the LV and left atrial filling pressures increase significantly during exercise, with an associated increase in pulmonary pressures leading to pulmonary congestion. Structural interventions to lower elevated either left or right atrial filling pressures are gaining attention.

Studies in heart failure show that lowering left atrial pressure may reduce cardiovascular events while improving functional capacity. The creation of an interatrial shunt has emerged as a therapy to decompress the left atrium in patients with acute and chronic heart failure. As such, attention has turned toward the development of interatrial shunt devices (IASDs) as a means of reducing the detrimental increase in left-sided filling pressures with exercise in an effort to improve symptomatology. IASDs may be used to treat various kinds of heart failure and/or other diseases that may result in too high of a pressure in the right atrium of a patient.

SUMMARY

Current IASDs reside in the interatrial septum, with risk for right-to-left shunting and systemic embolization. Moreover, preservation of the interatrial septum is important with an increasing number of left-sided transseptal transcatheter interventions. Ways to improve IASDs for safer and better procedures are needed.

According to some embodiments, a shunting catheter includes a catheter shaft including a shaft lumen and a side opening, and a tissue-removal assembly disposed in the shaft lumen in a first state and including a shunting shaft being extendable from the side opening of the catheter shaft. The shunting shaft has a curved shape when extending from the side opening to a second state, and the shunting shaft has an opening at a distal end thereof. The tissue-removal assembly includes a cutting component disposed at the distal end of the shunting shaft. In some embodiments, the cutting component can include ablation electrode(s) to deliver ablative energy. In some embodiments, the cutting component can include a mechanical coring edge (e.g., a cutting sheet).

According to some embodiments, a method of creating a shunt includes deploying a tissue-removal assembly in a shaft lumen of a catheter shaft at a first state, the tissue-removal assembly including a shunting shaft and a cutting component disposed at a distal end of the shunting shaft, operating the tissue-removal assembly to a second state, wherein the distal end of the shunting shaft extends from a side opening of the catheter shaft with a curved shape, disposing the cutting component approximate to a tissue wall of a patient, cutting, using the cutting component, the tissue wall, and removing an area of tissue from the tissue wall to form an opening in the tissue wall using the tissue-removal assembly.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
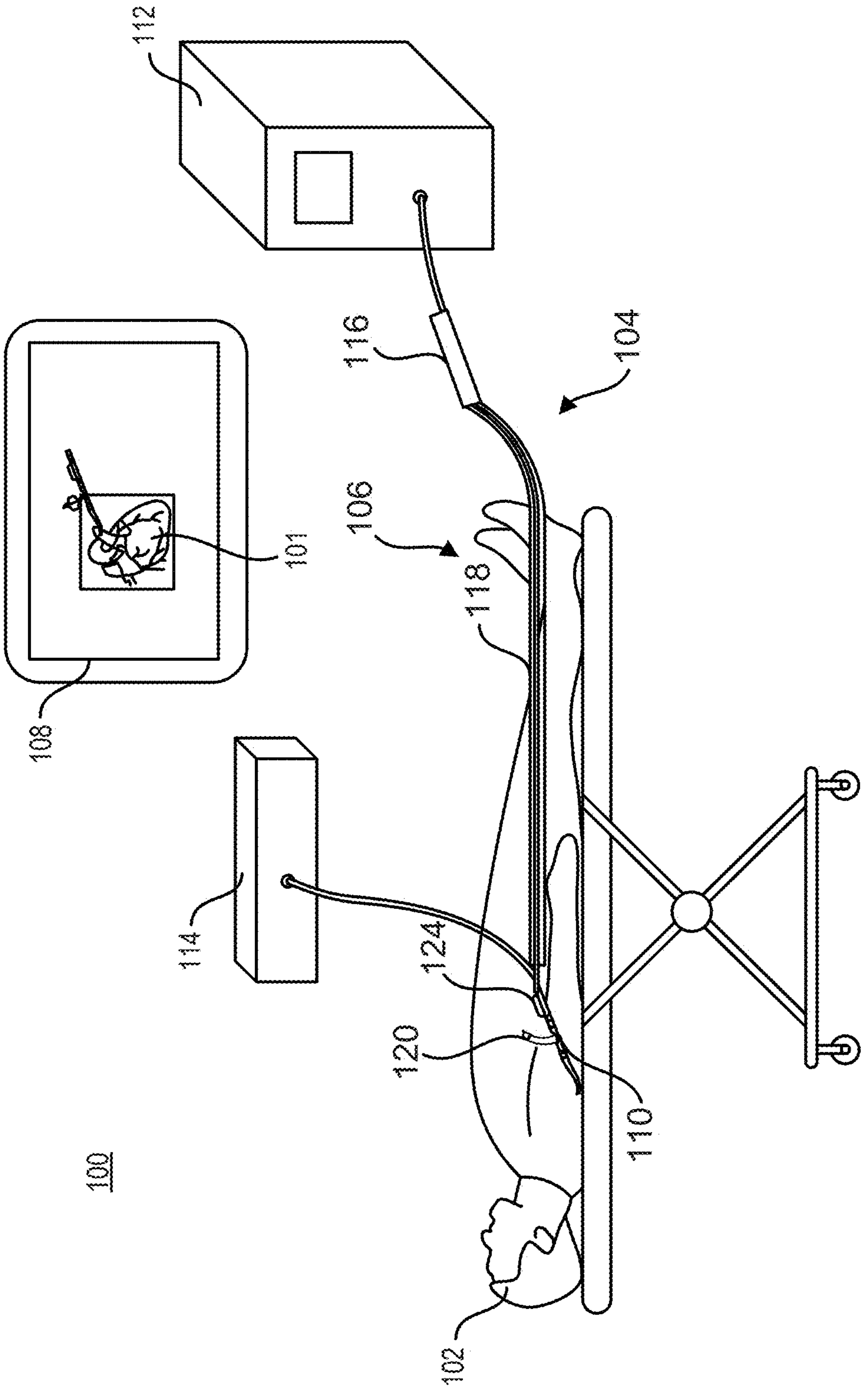
FIG. 1 is a diagram illustrating an exemplary clinical setting for treating a heart of a patient, using a shunting catheter system including a tissue-removal assembly, in accordance with embodiments of the present disclosure.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (e.g., 1 to 5 includes 1, 1.5, 2, 2.75, 3, 3.80, 4, and 5) and any number within that range.

Although illustrative methods may be represented by one or more drawings (e.g., flow diagrams, communication flows, etc.), the drawings should not be interpreted as implying any requirement of, or particular order among or between, various steps disclosed herein. However, some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information. In some embodiments, the term "receive" or "receiving" means obtaining from a data repository (e.g., database), from another system or service, from another software, or from another software component in a same software. In certain embodiments, the term "access" or "accessing" means retrieving data or information, and/or generating data or information.

There are various approaches for creating an interatrial shunt, which is a connection or gateway between the left and right atria of a patient's heart for blood to flow through. In some embodiments, examples of interatrial shunt devices (IASDs) include implants or shunting catheters. For example, devices reside in the interatrial septum, with risk for right-to-left shunting and systemic embolization. In some examples, preservation of the interatrial septum is important with an increasing number of left-sided transseptal transcatheter interventions. Ways to improve IASDs for safer and better procedures are needed. At least some embodiments of the present disclosure are directed to a shunting catheter for deployment through a patient's coronary sinus (CS) for creating a shunt between the CS and the patient's left atrium (LA). In some embodiments, a shunt is formed in the patient's CS vessel by removing an area of tissue to create an opening between the patient's CS and LA. At least some embodiments of the present disclosure are directed to a shunting catheter for deployment through a patient's atrial septum (AS) for atrial septal shunting.

A patient's CS ostium may have a diameter of from about 5 mm to about 25 mm. As the CS is a relatively small vessel, at least some embodiments of the present disclosure are directed to features of a shunting catheter that helps angle a tissue-removal assembly towards a patient's vessels during deployment to remove an area of tissue to create a shunt. In some embodiments, a shunting catheter includes a catheter shaft having a distal end and a proximal end. The catheter shaft includes a shaft lumen and a side opening. In some embodiments, a tissue-removal assembly is disposed in the shaft lumen in a first state and includes a shunting shaft having a distal end being extendable from the side opening of the catheter shaft. The distal end of the shunting shaft has a curved shape when extending from the side opening to a second state. In some embodiments, the tissue-removal assembly includes a cutting component disposed at the distal end of the shunting shaft. In some embodiments, the catheter shaft is made of flexible materials that bends according to the anatomy of the CS to conform to the shape of the patient's CS. In yet some embodiments, the catheter shaft includes a stabilizing element such as distal tip that has a curve (e.g., a pre-existing curve) conforming to the shape of a patient's CS to help stabilize the catheter and minimize potential damage to a patient's tissue wall (e.g., the vessel wall of a patient's CS).

In some embodiments, an apposition element is protruded from the catheter shaft during deployment to help stabilize the catheter at a desired location for creating the shunt. In certain embodiments, the shunting shaft of the tissue-removal assembly further includes a tube (e.g., a hypotube) to support the cutting component and one or more puncture elements connected to the shunting shaft. The tube may have a plurality of cuts along the tube to help facilitate bending of the tube. In certain embodiments, the shunting catheter is inserted through the patient's superior vena cava (SVC) via a transjugular approach. In certain embodiments, the shunting catheter is inserted through the patient's inferior vena cava (IVC) via a transfemoral approach.

FIG. 1 is a diagram illustrating an exemplary clinical setting 100 for treating a heart 101 of the patient 102, using a shunting catheter system 104, in accordance with embodiments of the present disclosure. The shunting catheter system 104 includes a shunting device 106 including a tissue-removal assembly 120 configured to remove an area of tissue from a tissue wall. As will be appreciated by the skilled artisan, the clinical setting 100 may have other components and arrangements of components that are not shown in FIG. 1. In some embodiments, the shunting catheter system 104 includes or is coupled to an imaging system (e.g., an X-ray system) which may include one or more visualization elements and a display 108. In some embodiments, one or more visualization elements may be disposed on the shunting device 106. In certain embodiments, the imaging system can help guide a physician's operation of the shunting catheter 110 during procedure.

The shunting device 106 includes a shunting catheter 110, a controller 112, and an energy source 114 (e.g., a generator). The controller 112 is configured to control functional aspects of the shunting device 106. In embodiments, the controller 112 is configured to control the energy source 114 to deliver energy to the shunting catheter 110. The controller 112 may be connected to the one or more visualization elements to facilitate positioning of the shunting catheter 110 in a patient's heart during procedure. In some embodiments, the energy source 114 is connected to the controller 112. In yet some embodiments, the energy source 114 may be incorporated into the controller 112.

According to some embodiments, a tissue-removal assembly 120 can be delivered by the shunting catheter 110 to remove an area of tissue from a tissue wall and create a shunt. The tissue-removal assembly 120 can be advanceable inside a lumen of the shunting catheter 110 and extendable from a side opening of the shunting catheter 110 to form a curved shape. The tissue-removal assembly 120 can include a cutting component disposed at the distal end thereof to capture, cut, and/or collect an area of tissue from the tissue wall and create the shunt.

As will be appreciated by the skilled artisan, the depiction of the shunting catheter system 104 shown in FIG. 1 is intended to provide a general overview of the various components of the shunting catheter system 104 and is not in any way intended to imply that the disclosure is limited to any set of components or arrangement of the components. For example, the skilled artisan will readily recognize that additional hardware components, e.g., breakout boxes, workstations, and the like, can and likely will be included in the shunting catheter system 104.

According to some embodiments, the shunting device 106 includes a handle 116, a catheter shaft 118, the tissue-removal assembly 120 configured to remove an area of tissue from a tissue wall. In some embodiments, the tissue-removal assembly 120 can include a puncture element (e.g., a puncture needle) configured to puncture through the tissue wall. In certain embodiments, the puncture element may be curved. In some instances, the puncture element may be curved or angled to bias a distal tip of the puncture element towards a tissue wall of the patient 102. In certain embodiments, the tissue-removal assembly 120 is connected to the energy source 114 to provide shunting. For example, the tissue-removal assembly 120 includes electrodes to receive electrical power from the energy source 114 to deliver ablation energy to the target location (e.g., a target tissue) at a cardiovascular system (e.g., a circulatory system) wall. In certain embodiments, the handle 116 is configured to be operated by a user to position the tissue-removal assembly 120 at the desired anatomical location. The catheter shaft 118 generally defines a longitudinal axis of the shunting catheter 110. In some embodiments, the tissue-removal assembly 120 may be connected to a shunting shaft positioned within the catheter shaft 118 at a first state (e.g., before a deployment and/or during a deployment to position the tissue-removal assembly 120). In certain embodiments, the shunting shaft has a pre-determined curve. In some examples, the shunting shaft has a pre-determined curve for the tissue-removal assembly to deploy. In certain embodiments, the shunting shaft is extended from the catheter shaft 118 at a second state (e.g., a puncture state to puncture through a tissue wall of a patient) and/or a third state (e.g., a state to cut, remove, and/or collect an area of tissue).

According to certain embodiments, during deployment, the shunting device 106 including the catheter shaft 118 enters through a patient's CS ostium located in the patient's right atrium. The shunting device 106 may then be oriented through one or more mechanisms in the patient's CS, as will be discussed in more details below. In some embodiments, in order to conform to the shape of the patient's CS, the catheter shaft 118 is made of flexible materials that may bend according to the anatomy of the CS.

In certain embodiments, the shunting catheter 110 can include an optional apposition element 124 disposed proximate to the tissue-removal assembly 120. In some embodiments, the apposition element is disposed within a shaft (e.g., an outer shaft) at the first state. In some embodiments, the apposition element 124 is protruded from the catheter shaft 118 at the first state, the second state, and/or the third state. In certain embodiments, the apposition element 124 can appose to a cardiovascular system wall (e.g., the front wall or back wall of the CS, a left atrium wall, a right atrium wall, etc.) at the second state and/or third state, for example, to help position and/or stabilize the tissue-removal assembly 120. In certain embodiments, the apposition element 124 includes a braid structure. In some embodiment, the apposition element 124 may include a nitinol braid that can be held within the catheter shaft 118.

According to some embodiments, various components (e.g., the controller 112) of the shunting catheter system 104 can be implemented on one or more computing devices. A computing device may include any type of computing device suitable for implementing embodiments of the disclosure. Examples of computing devices include specialized computing devices or general-purpose computing devices such as workstations, servers, laptops, portable devices, desktop, tablet computers, hand-held devices, general-purpose graphics processing units (GPGPUs), and the like, all of which are contemplated within the scope of FIG. 1 with reference to various components of the shunting catheter system 104.

In some embodiments, a computing device (e.g., the controller 112) includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices. In some embodiments, various components or parts of components (e.g., controller 112, shunting catheter 110, etc.) can be integrated into a physical device.

In some embodiments, the shunting catheter system 104 includes one or more memories (not illustrated). The one or more memories includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the one or more memories store computer-executable instructions for causing a processor (e.g., the controller 112) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

In some embodiments, the memory may include a data repository which may be implemented using any one of the configurations described below. A data repository may include random access memories, flat files, XML files, and/or one or more database management systems (DBMS) executing on one or more database servers or a data center. A database management system may be a relational (RDBMS), hierarchical (HDBMS), multidimensional (MDBMS), object oriented (ODBMS or OODBMS) or object relational (ORDBMS) database management system, and the like. The data repository may be, for example, a single relational database. In some cases, the data repository may include a plurality of databases that can exchange and aggregate data by a data integration process or software application. In an exemplary embodiment, at least part of the data repository may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the shunting catheter system 104 can communicate via or be coupled to via a communication interface, for example, a wired or wireless interface. The communication interface includes, but is not limited to, any wired or wireless short-range and long-range communication interfaces. The wired interface can use cables, umbilicals, and the like. The short-range communication interfaces may be, for example, local area network (LAN), interfaces conforming to known communications standards, such as Bluetooth™ standard, IEEE 802 standards (e.g., IEEE 802.11), or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet. Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

Figure 2:
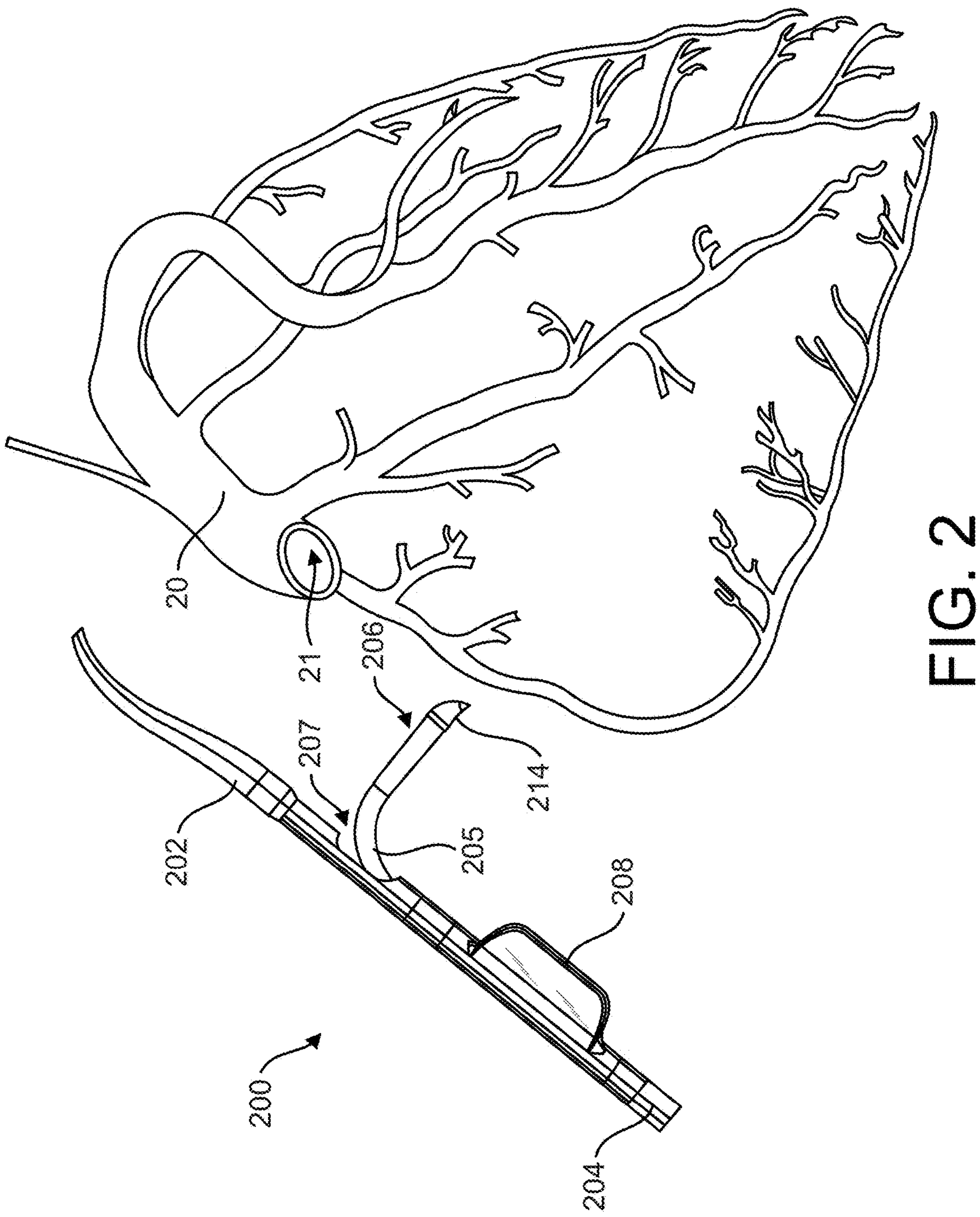
FIG. 2 is a schematic diagram illustrating an example of a shunting device including a tissue-removal assembly to be deployed in a heart of a patient, in accordance with embodiments of the present disclosure.

FIG. 2 is a schematic diagram illustrating an example of a shunting device 200 to be deployed in a heart of a patient, in accordance with embodiments of the present disclosure. FIG. 2 is merely an example. One of the ordinary skilled in the art would recognize many variations, alternatives, and modifications. As shown, the shunting device 200 includes a shunting catheter 202 to be delivered through a patient's coronary sinus (CS) 20 via the CS ostium 21. In some embodiments, the shunting catheter 202 includes a catheter shaft 204, an optional apposition element 208, and a tissue-removal assembly 206. In certain embodiments, the catheter shaft 204 receives a shunting shaft 205 which has a curve when extends out of a shaft opening 207. In some embodiments, as illustrated, the shunting shaft 205 is extended from the catheter shaft 204 at a second state (e.g., a puncturing state) and/or a third state (e.g., a state to cut, remove, and/or collect an area of tissue). In certain examples, the shunting shaft 205 forms an angle greater than 30 degrees from a longitudinal axis of the catheter shaft 204. In some embodiments, the shunting shaft 205 forms an angle proximate to 90 degrees from the catheter shaft 204. In some embodiments, the shunting shaft 205 forms an angle in the range of 60 degrees to 120 degrees from the catheter shaft 204.

In some embodiments, the tissue-removal assembly 206 is extended from the catheter shaft 204 at a second state (e.g., a state to puncture a tissue wall and/or remove an area of tissue from the tissue wall). According to some embodiments, the tissue-removal assembly 206 includes a puncture element 214 having a tip defining a distal point of the puncture element 214 and a blade section. In some embodiments, the blade section of the puncture element has a tapered shape and includes a blade edge.

In some embodiments, the puncture element 214 of the tissue-removal assembly 206 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient).

In some embodiments, the catheter shaft 204 is made of flexible material that may curve with the anatomy of the patient's CS 20. In certain embodiments, for example, the catheter shaft 204 may include polyether block amide, nylon, silicone, or a combination thereof. In some embodiments, the catheter shaft 204 can include a laser cut hypotube (LCHT) that may have a specific cut pattern to allow formation of the shaft opening 207. In some instances, the catheter shaft 204 may be a multi-layered and multi-material component. In some examples, the catheter shaft 204 is reinforced with a braid and can have an etched or casted liner. The braid for reinforcing the catheter shaft 204 may be made of, for example, stainless steel, nitinol, rigid plastics, and the like. The liner may be made from polyetheretherketone (PEEK), polytetrafluoroethylene (PTFE), copolymers of polyamide and polyether, polyether block amid (PEBAX), or a combination thereof. In some embodiments, the catheter shaft 204 is coated for lubricity with a hydrophilic coating, or other types of coating suitable for coating a catheter shaft as known by a skilled person in the art.

In some embodiments, the shunting catheter 202 has a diameter of from about 2 mm to about 8 mm. In certain embodiments, the shunting catheter 202 has a diameter of from about 3 mm to about 7 mm. In some embodiments, the shunting catheter has a diameter of from about 4 mm to about 6 mm. In certain embodiments, the shunting catheter 202 may have a diameter allowing it to pass through vessels and parts of the cardiovascular system to reach a target location.

Figure 3:
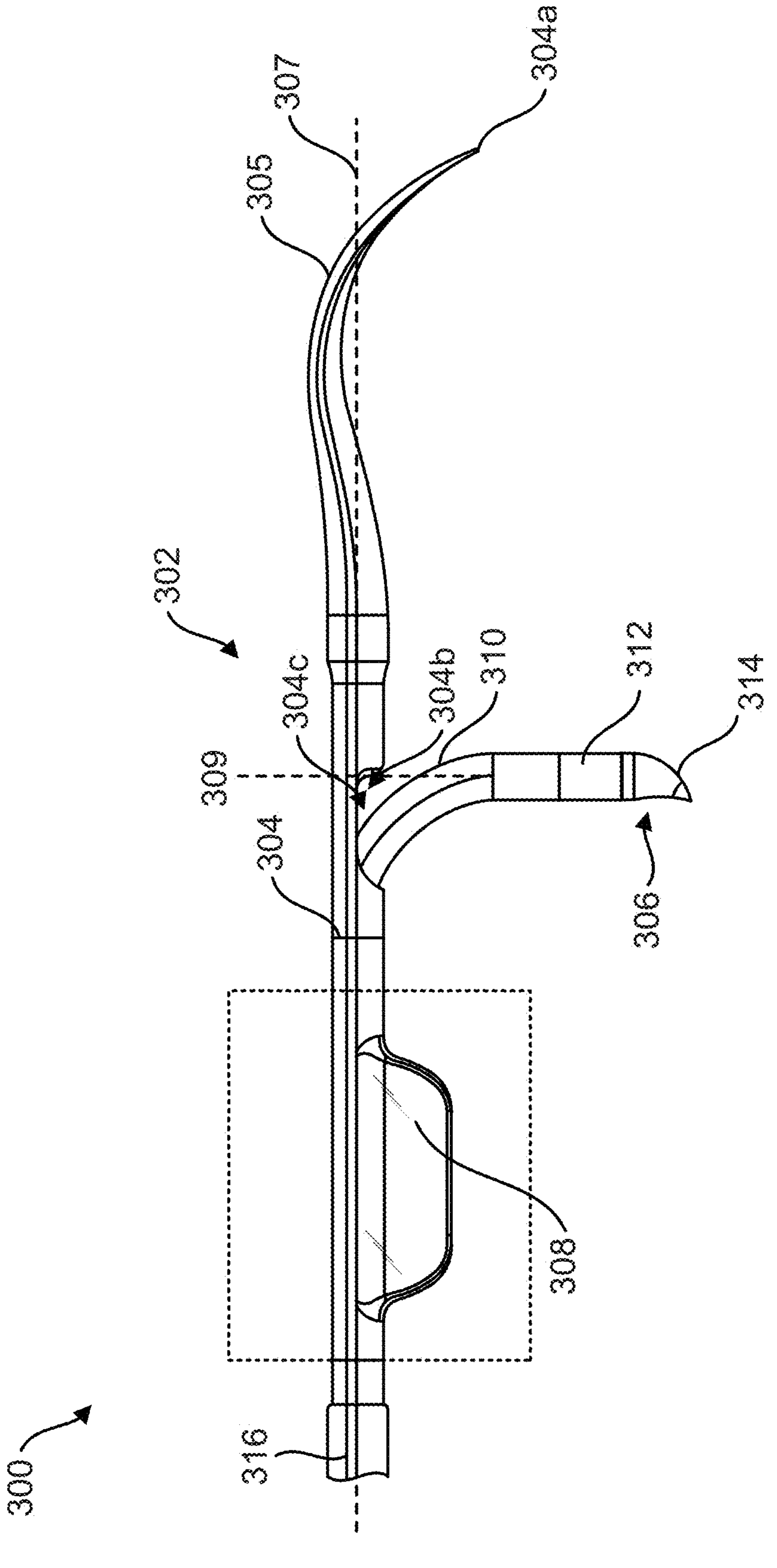
FIG. 3 is a schematic diagram of a side view of an example of a shunting device including a tissue-removal assembly, in accordance with embodiments of the present disclosure.

FIG. 3 is a schematic diagram of a side view of an example of a shunting device 300 and a perspective view of an optional apposition element 308 of the shunting device 300, in accordance with embodiments of the present disclosure. FIG. 3 is merely an example. One of the ordinary skilled in the art would recognize many variations, alternatives, and modifications. As shown, in some embodiments, the shunting device 300 includes a shunting catheter 302 to be delivered through a patient's coronary sinus (CS) (e.g., the CS 20 of FIG. 2). In certain embodiments, the shunting catheter 302 includes an apposition element 308, a catheter shaft 304, and a tissue-removal assembly 306 including a puncture component 314.

According to certain embodiments, the catheter shaft 304 has a distal end 304*a*, a proximal end (not shown), and a shaft lumen 304*b*. In some embodiments, the catheter shaft 304 is made of flexible material that may curve with the anatomy of the patient's CS. In certain embodiments, the catheter shaft 304 may include polyether block amide, nylon, silicone, and/or a combination thereof. In some instances, the catheter shaft 304 may be a multi-layered and multi-material component. In some examples, the catheter shaft 304 is reinforced with a braid and can have an etched or casted liner, and/or a laser cut hypotube (LCHT). The braid for reinforcing the catheter shaft 304 may be made of stainless steel, nitinol, rigid plastics, and the like. The liner may be made from polyetheretherketone (PEEK), polytetrafluoroethylene (PTFE), copolymers of polyamide and polyether, or a combination thereof. In certain embodiments, the catheter shaft 304 may be injection molded or extruded. In some embodiments, the catheter shaft 304 can include a laminated structure formed of multiple layers including, for example, a liner, a reinforcement braid or LCHT, and extrusions melted together. In some embodiments, the catheter shaft 304 is coated for lubricity with a hydrophilic coating, or other types of coating suitable for coating a catheter shaft as known by a skilled person in the art. In some instances, the catheter shaft 304 may have multiple lumens.

According to some embodiments, the catheter shaft 304 may include a stabilizing element such as distal tip 305 at the distal end 304*a* that has a curve (e.g., a pre-existing curve), for example, a curve conforming to the anatomy of a patient's CS. In some instances, the distal tip 305 may be made of a different material than other parts of the catheter shaft 304. In some instances, for example, the distal tip 305 may be made of a material more flexible than the material of other parts of the catheter shaft 304. The distal tip 305 may be injection molded or machined to have a unique geometry (e.g., a curve) for better stabilizing the catheter shaft 304 during deployment.

According to some embodiments, the distal tip 305 may have a length of from about 5 mm to about 85 mm. In certain embodiments, the catheter shaft 304 includes a shaft opening 304*c*. In some embodiments, a portion of the catheter shaft from the shaft opening 304*c* and the distal end 304*a* has a curve. In some embodiments, the catheter shaft 304 defines a first axis 307, and the tissue-removal assembly 306 defines a second axis 309 at the second state after deployment. In certain embodiments, the second axis 309 and the first axis 307 form an angle greater than zero degree.

According to certain embodiments, the tissue-removal assembly 306 is disposed in the shaft lumen 304*b* at a first state (e.g., before a deployment and/or during a deployment to position the tissue-removal assembly 306). In certain embodiments, the tissue-removal assembly 306 can be connected to a shunting shaft 310 positioned within the shaft lumen 304*b* of the catheter shaft 304 at a first state. In certain embodiments, the shunting shaft 310 has a pre-determined curve. In some examples, the shunting shaft 310 has a pre-determined curve for the tissue-removal assembly 306 to deploy. In certain embodiments, the shunting shaft is extended from the shaft lumen 304*b* of the catheter shaft 304 at a second state (e.g., a puncturing state to puncture through a tissue wall of a patient) and/or a third state (e.g., a state to cut, remove, and/or collect an area of tissue).

In some embodiments, an optional expandable element 312 may be coupled to the catheter shaft 304. The expandable element 312 may be a balloon or a basket configured to be expanded when the tissue-removal assembly 306 is at a third state (e.g., a state to cut, remove, and/or collect an area of tissue). The expandable element 312 can include a cutting component configured to cut an area of tissue from a tissue wall. In some embodiments, the cutting component can include ablation electrode(s) to deliver ablative energy. In some embodiments, the cutting component can include a mechanical coring edge (e.g., a cutting sheet). In some embodiments, the expandable element 312 can be expanded to form a basket structure adjacent to the cutting component thereof. The cutting component can be positioned between the expandable component 312 and the puncture component 314.

According to certain embodiments, the puncture component 314 is disposed in the shaft lumen 304*b* at a first state. The puncture component 314 may be connected to the tissue-removal assembly 306 positioned within the shaft lumen 304*b* of the catheter shaft 304 at a first state (e.g., before a deployment and/or during a deployment to position the tissue-removal assembly 306).

In some embodiments, the puncture component 314 (e.g., along with the tissue-removal assembly 306) is extended from the catheter shaft 304 at a second state (e.g., a puncturing state to puncture through a tissue wall). According to some embodiments, the puncture component 314 includes a puncture element having a tip defining a distal point of the puncture element and a blade section. In some embodiments, the blade section of the puncture element has a tapered shape and includes a blade edge. For example, the blade section has a distal end at the blade edge and a proximal end close to the expandable element 312, with the blade section at the proximal end having a first thickness and the blade section at the distal end having a second thickness, where the second thickness is smaller than the first thickness. In some embodiments, a distal end of the blade edge is the tip of the puncture element. In certain embodiments, the blade section includes two flat surfaces, where the intersection of the two flat surfaces defines the blade edge, and a curved surface surrounding the two flat surfaces (see e.g., FIG. 9B).

In some embodiments, the puncture element of the puncture component 314 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall of a patient).

In certain embodiments, the puncture component 314 has a pre-determined curve. In some embodiments, the puncture component 314 may form an angle proximate to 90 degrees from the catheter shaft 304. In some embodiments, the puncture component 314 may form an angle in the range of 60 degrees to 120 degrees from the catheter shaft 304. In certain embodiments, the puncture component 314 is extended from the shaft lumen 304*b* of the catheter shaft 304 at a second state (e.g., a puncturing state to use the puncture element on a distal end of the puncture component 314). In some examples, the puncture component 314 may include one or more electrodes configured to deliver ablative energy when the puncture component 314 is at a second state. In certain examples, the puncture component 314 may include a puncture element made of conductive material and configured to deliver ablative energy when the puncture component 314 is at a second state.

According to some embodiments, the shunting catheter 302 further includes an outer shaft 316 disposed outside of at least a part of the catheter shaft 304 during deployment. In some embodiments, the outer shaft 316 is made of flexible material that may curve with the anatomy of the patient's CS. In certain embodiments, for example, the outer shaft 316 may include polyether block amide, nylon, silicone, or a combination thereof. In some instances, the outer shaft 316 may be a multi-layered and multi-material component. In some examples, the outer shaft 316 is reinforced with a braid and/or can have an etched or casted liner. The braid for reinforcing the catheter shaft 304 may be made of stainless steel, nitinol, rigid plastics, and the like. The liner may be made from polyetheretherketone (PEEK), polytetrafluoroethylene (PTFE), copolymers of polyamide and polyether, or a combination thereof. In certain embodiments, the outer shaft 316 may be injection molded or extruded. In some embodiments, the catheter shaft 304 is coated for lubricity with a hydrophilic coating, or other types of coating suitable for coating a catheter shaft as known by a skilled person in the art.

According to certain embodiments, the apposition element 308 is disposed within the outer shaft 316 at a first state (e.g., during deployment). In embodiments, the apposition element 308 protrudes from the catheter shaft 304 during deployment. The apposition element 308 is flexible and compressed to fit within the outer shaft 316 and configured to decompress and protrude from the catheter shaft 304 during deployment. In some embodiments, the apposition element 308 is disposed proximate to the tissue-removal assembly 306 and/or the one or more shaft openings 304*c*. In some instances, the apposition element 308 is a braided structure including one or more metal wires such as, for example, nitinol wires, stainless steel wires, and the like. In yet some instances, the apposition element 308 is made of a flexible material having a portion protruding from the catheter shaft 304. In some examples, the flexible material may be a foam. In some instances, the flexible material may be a balloon filled with a contrast solution that shows up under fluoroscopy. In yet some instances, the flexible material may be a polymer with a radiopaque marker added for visualization. The radiopaque marker may include tantalum, gold, or any radiopaque marker known by a skilled person in the art.

In certain embodiments, the optional apposition element 308 can be configured to appose a patient's tissue wall (e.g., the vessel wall of a patient's CS or LA) such that the shunting catheter 302 is stabilized in one position once deployed.

Figure 4:
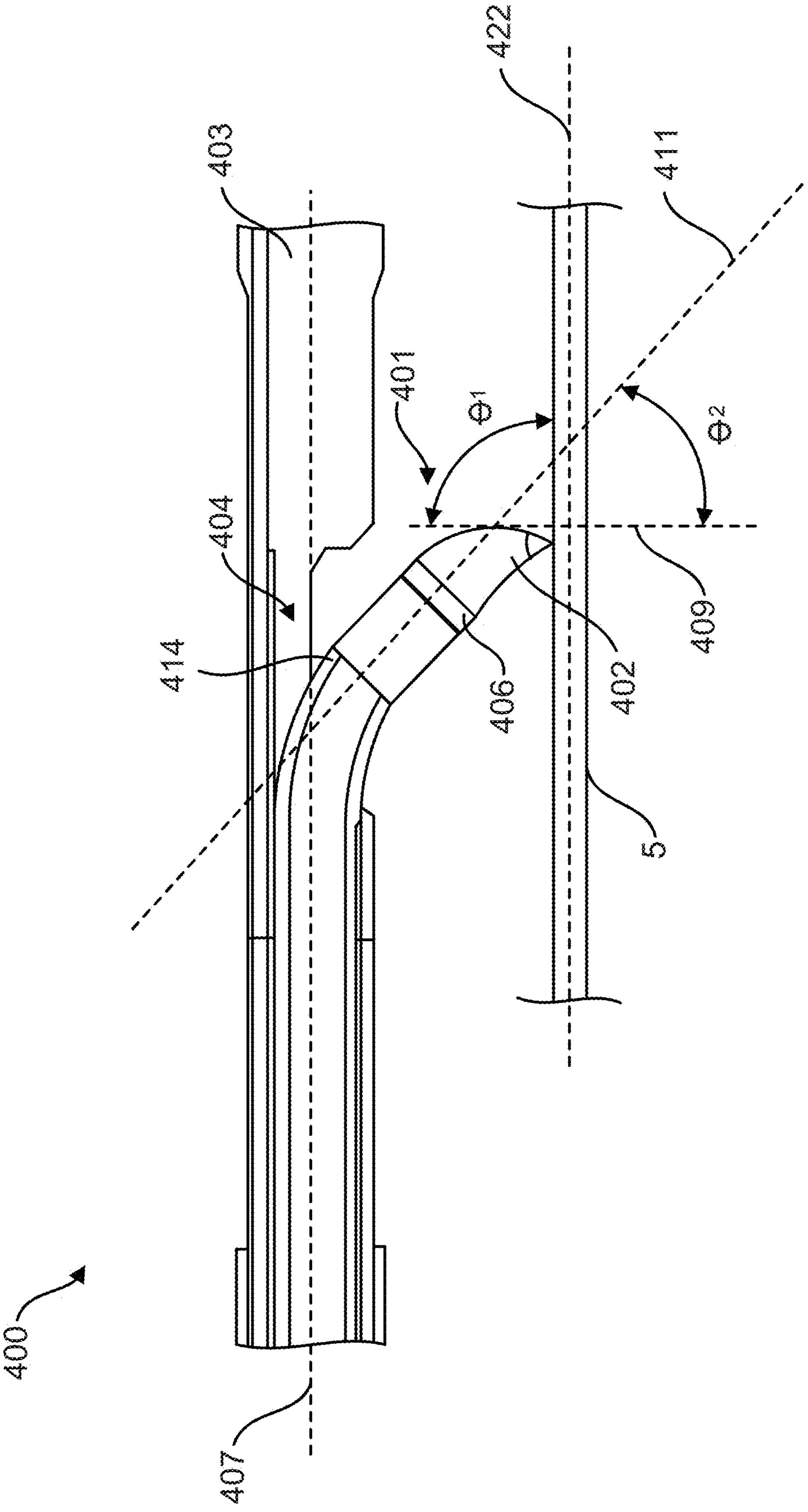
FIG. 4 is a schematic diagram of a cross-sectional view of an example of a shunting catheter and a side view of a tissue-removal assembly including a puncture element forming an angle with respect to a tissue wall, in accordance with embodiments of the present disclosure.

FIG. 4 is a schematic diagram of a cross-sectional view of an example of a shunting catheter 400 and a side view of an example puncture element 402 forming an angle $\theta_1$ with respect to a tissue wall 5, in accordance with embodiments of the present disclosure. The shunting catheter 400 includes a catheter shaft 403 having a shaft lumen 404, and a tissue-removal assembly 401 disposed within the shaft lumen 404 at a first state (e.g., during deployment).

In some embodiments, the tissue-removal assembly 401 includes a cutting component 406 coupled to a distal portion of a shunting shaft 414 which is advanceable inside the shaft lumen 404.

In certain embodiments, a distal portion of the shunting shaft 414 is extended from a side opening of the catheter shaft 403 at a second state. The tissue-removal assembly 401 may include a dilator (not shown). The dilator may be connected to a puncture element shaft (extendable inside a lumen of the shunting shaft 414, not shown) on one end, and a puncture element 402 (e.g., a needle) on the other end. In some embodiments, the puncture element 402 may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall 5 of a patient) to facilitate puncturing through a tissue wall 5. In some embodiments, the dilator may be configured to deliver energy, or include one or more electrodes configured to deliver energy (e.g., ablative energy, radiofrequency (RF) energy, phased RF energy, thermal energy, cryogenic energy, pulse ablative energy, (e.g., pulsed field ablation (PFA)), microwave energy, laser energy, ultrasound energy, etc.) to target tissue (e.g., a tissue wall 5 of a patient).

In some embodiments, the tissue-removal assembly 401 is positioned within the catheter shaft 403 at a first state (e.g., before a deployment and/or during a deployment to position the tissue-removal assembly 401). In certain embodiments, a distal portion of the shunting shaft 414 has a pre-determined curve. In some examples, the curved distal portion of the shunting shaft 414 is directly adjacent or in close proximity with the tissue-removal assembly 401. In certain embodiments, the shunting shaft 414 is extended from the catheter shaft 403 at a second state (e.g., a puncturing state to puncture tissue wall 5). In certain embodiments, the shunting shaft 414 may not have a predetermined curve and can be made of an at least semi-malleable material that may allow a physician to manipulate the distal portion of the shunting shaft 414 into a curve. The curve of the shunting shaft 414 may facilitate directing the puncture element 402 towards the tissue wall 5 at the second state during a puncturing procedure and/or at a third state during a tissue-removal procedure. In certain embodiments, the tissue-removal assembly 401, including a distal portion of the shunting shaft 414, is extended from the catheter shaft 403 at a second state (e.g., a puncturing state to use the puncture element 402) and/or a third state (e.g., a cutting state to use a cutting component 406). In certain embodiments, the puncture element 402 has a predetermined curve. The curve of the puncture element 402 may bias the puncture element 402 (e.g., a tip thereof) towards the tissue wall of the patient at the second state or third state during a puncturing or tissue-removal procedure.

According to some embodiments, the catheter shaft 403 includes a shaft opening. In some embodiments, the catheter shaft 403 defines a first axis 407, and where the tip of the puncture element 402 contacts a tissue wall 5 defines a second axis 409. In certain embodiments, the second axis 409 and the first axis 407 form an angle greater than zero degrees. In certain examples, the second axis 409 and the first axis 407 form an angle greater than 30 degrees. In some embodiments, the second axis 409 and the first axis 407 form an angle proximate to 90 degrees. In some embodiments, the second axis 409 and the first axis 407 form an angle in the range, for example, from 60 degrees to 120 degrees. In some instances, the puncture element 402 includes a pre-curve formed from a semi-rigid or rigid material. The semi-rigid or rigid material of the puncture element 402 may include nitinol or stainless steel (SS) with a curve built in before deployment.

In some embodiments, the shunting shaft 414 includes a curved portion that forms an arc connecting a first straight portion of the shunting shaft 414 disposed inside the shaft lumen 404 and a second straight portion of the shunting shaft 414 extended outward from the shaft lumen 404, the second straight portion of the shunting shaft 414 defines an axis 411. In embodiments, for example as shown, the curved portion of the shunting shaft 414 is adjacent a shaft opening. In certain embodiments, a dilator can be located at the end of the second straight portion of the shunting shaft 414 and outside of the curved portion of the shunting shaft 414. In some embodiments, the puncture element 402 includes a curve, thus having a concave shape on one side of the puncture element 402, and a convex shape on the other side of the puncture element 402. As shown, the curve of the puncture element 402 is configured to bias the tip of the puncture element 402 away from the axis 411 and towards the tissue wall 5. In certain embodiments, the axis 409 and axis 411 defines an angle $\theta_2$. In some embodiments, the angle $\theta_2$ may be above zero degrees and below 180 degrees. In some embodiments, the angle $\theta_2$ may be above zero degrees and below 90 degrees.

In certain embodiments, the shunting catheter 400 includes multiple compartments (e.g., lumens) for various elements to provide more targeted control during deployment. For example, the shunting catheter 400 may include an additional lumen in between the catheter shaft 403 and the shunting shaft 414 for more precise control during deployment of the tissue-removal assembly 401. In some embodiments, the shunting catheter 400 may include lumens for containing functional components such as a guidewire or pull wire assembly. In yet some embodiments, the shunting catheter 400 may include additional lumens for holding shunted tissue from a tissue wall.

In some embodiments, the angle between the second axis 409 and the first axis 407 may be a result of the curve in shunting shaft 414 and a curve of puncture element 402, where the curve of the puncture element 402 further biases the puncture element 402 towards the tissue wall 5. Therefore, the angle $\theta_1$ between the second axis 409 and a third axis 422 defined by the tissue wall 5 may also result from the curve in shunting shaft 414 and the curve of puncture element 402. When a puncture assembly is extended from a catheter shaft at a second state or a third state, the distance between an outer surface of the catheter shaft and a surface of a patient's tissue wall (e.g., an inner surface of the vessel wall of a patient) may be small enough that a crimp shaft is prevented from curving more than a certain amount. This may result in the angle $\theta_1$ being greater than 90 degrees and preventing a tip of a puncture element from catching on, and puncturing through, the tissue wall at the intended target location. Instead, the tip of the puncture element may slide along the tissue wall before puncturing through, potentially damaging more of the tissue wall than intended and puncturing through the tissue wall at a different location than the target location. In some embodiments, the curved nature of puncture element 402 may bias the tip of puncture element 402 towards tissue wall 5 such that the angle $\theta_1$ between the second axis 409 (defined by the tip of the puncture element 402) and the third axis 422 is closer to 90 degrees. When the angle $\theta_1$ is closer to 90 degrees, puncture element 402 may more easily pierce through the tissue wall 5, preventing excess damage to the tissue wall 5 from dragging, and puncturing the tissue wall 5 more accurately at the target location.

In some embodiments, the tissue-removal assembly 401 includes a tube (e.g., a hypotube) to support the shunting shaft 414. The tube may include a plurality of laser cuts generally perpendicular to longitudinal axis defined by shunting shaft 414. In some embodiments, the tube may be formed of a conductive material configured to transmit energy to one or more electrodes on the tissue-removal assembly 401 to transmit energy to puncture tissue of a patient. In some instances, the tube can be made of stainless steel or nitinol. In certain instances, the tube may further include a pull wire assembly to control the flex or angle of the shunting shaft 414 and/or the puncture element 402 relative to the catheter shaft 403. The pull wire assembly may be laser welded to the tube or inside the tube at a distal end of the tube. In some embodiments, the pull wire assembly may include nitinol, stainless steel (SS), cobalt, chromium, titanium, or a combination thereof.

The shunting shaft 414 may be made of a semi-rigid or rigid material to have a pre-formed angle before deployment. After the tissue-removal assembly 401 is deployed, the pre-formed angle may be further adjusted using the pull wire assembly to further adjust and/or stabilize the contact point between the puncture element 402 and the tissue wall 5. In some embodiments, the shunting shaft 414 may be made of a semi-malleable material, where the curve in the shunting shaft 414 is formed in response to manipulation of the pull wire to adjust and/or stabilize the contact point between the puncture element 402 and the tissue wall 5.

In certain embodiments, during deployment, the guidewire may be used to guide the shunting catheter 400 into the CS of a patient. In yet certain embodiments, the guidewire may be used to indicate the location of the shunting catheter including one or more of the components (e.g., the puncture assembly, the shaft opening of the shunting catheter 400, etc.) in the CS of a patient.

Figure 5A:
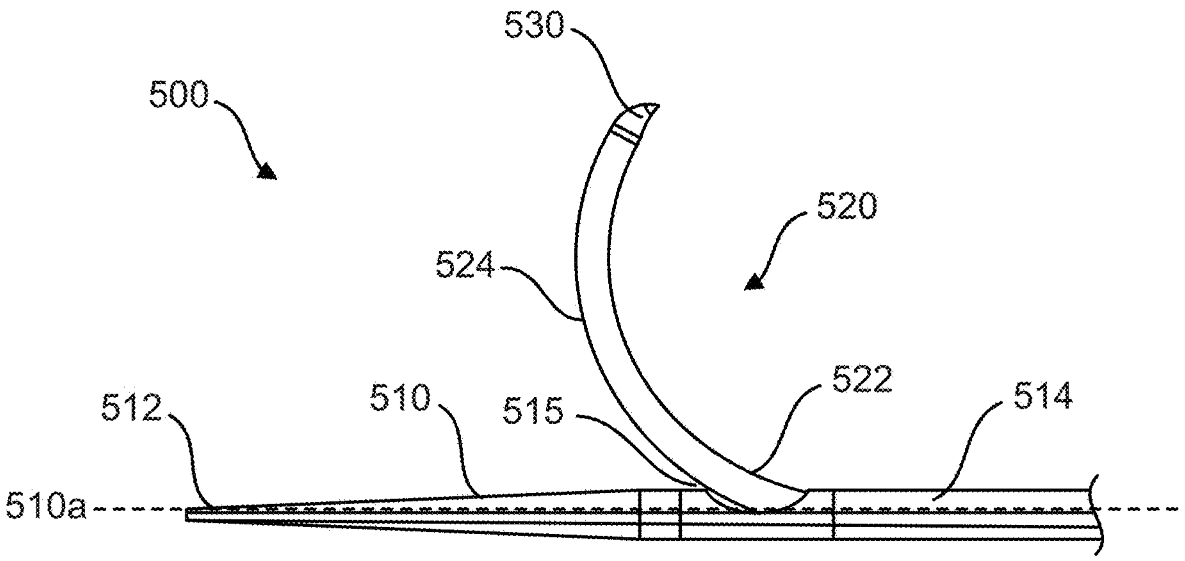
FIG. 5A is a schematic diagram illustrating an example of a tissue-removal assembly, in accordance with embodiments of the present disclosure.
Figure 5B:
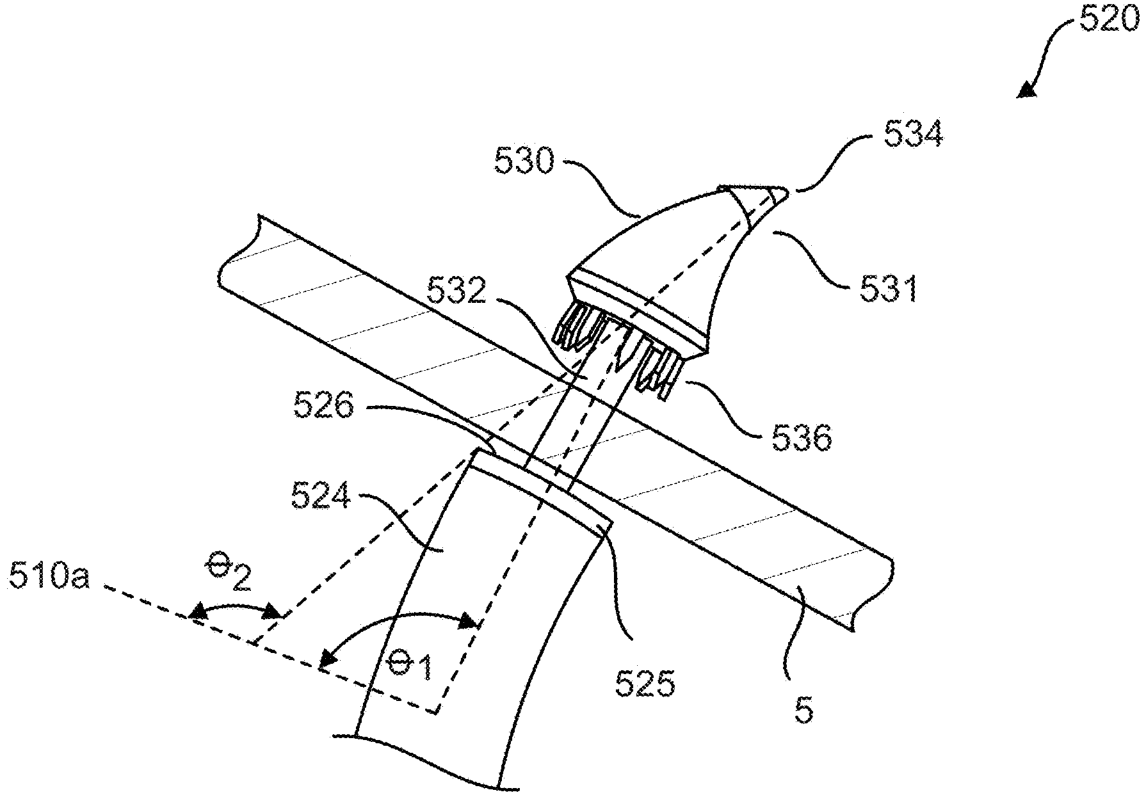
FIGS. 5B-5D are schematic diagrams of side views of the tissue-removal assembly of FIG. 5A in a process to create a shunt in a tissue wall, in accordance with embodiments of the present disclosure.
Figure 5C:
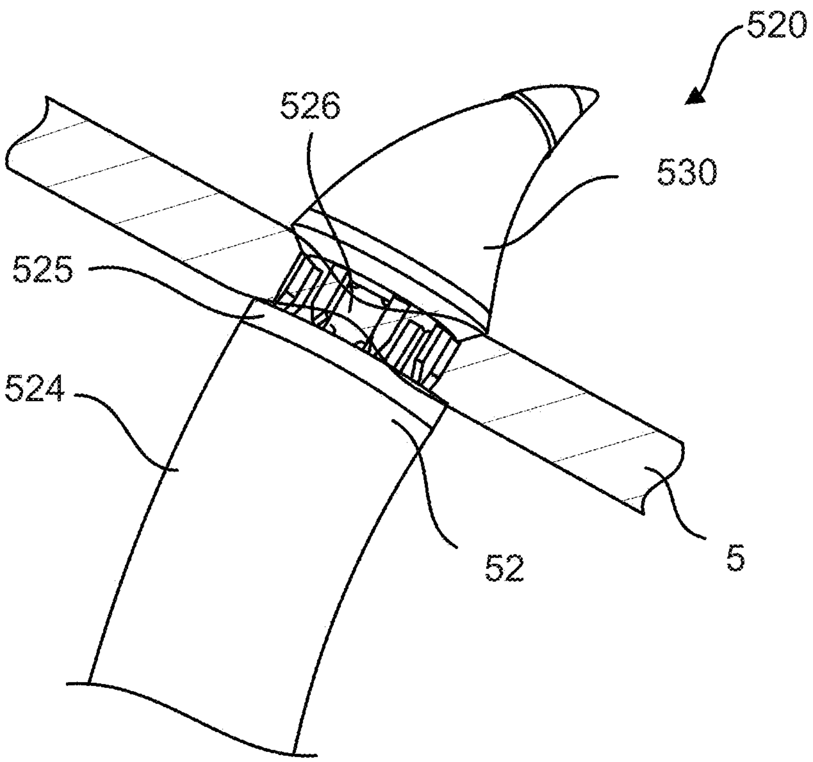
Figure 5D:
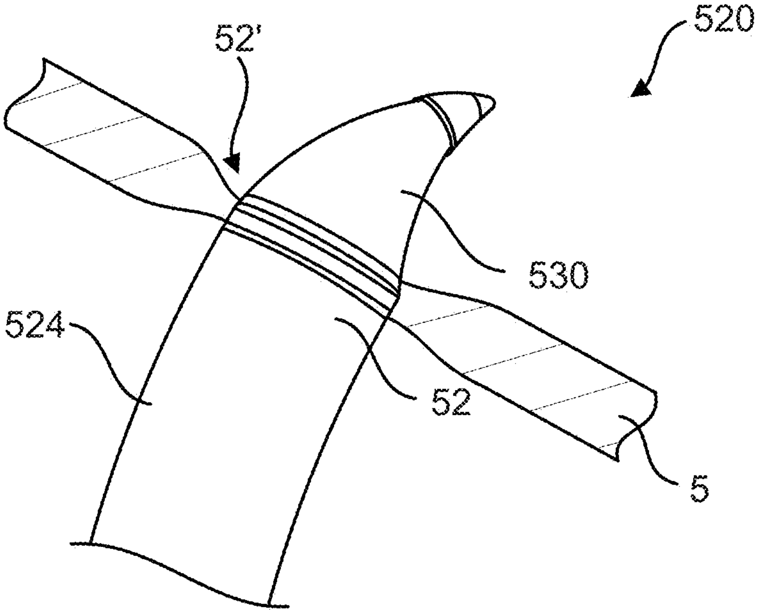

FIG. 5A is a schematic diagram illustrating an example of a shunting catheter 500 including a tissue-removal assembly 520, in accordance with some embodiments of the present disclosure. FIGS. 5B-5D are schematic diagrams of side views of the shunting catheter 500 of FIG. 5A which is deployed to create a shunt in a tissue wall 5 utilizing the tissue-removal assembly 520. According to some embodiments, the shunting catheter 500 includes a catheter shaft 510 having a distal end 512 and a proximal end (not shown). The catheter shaft 510 includes a shaft lumen 514 and a side opening 515 in communication with the shaft lumen 514. The tissue-removal assembly 520 includes a shunting shaft 522 having a distal portion 524 being extendable from the side opening 515 of the catheter shaft 510. Before the tissue-removal assembly 520 is deployed for tissue removal, the distal portion 524 of the shunting shaft 522 is received inside the shaft lumen 514 at a first state. When the tissue-removal assembly 520 is deployed for tissue removal, the distal portion 524 of the shunting shaft 522 can extend from the side opening 515 of the catheter shaft 510 to form a curved shape with a first curvature.

In some embodiments, the distal portion 524 of the shunting shaft 522 is formed of nitinol. It is to be understood that the distal portion 524 of the shunting shaft 522 can be formed of any suitable material (e.g., stainless steel, platinum iridium, thermoplastic, PEEK, and the like) configured to be self-bending/bendable to form a curved shape. For example, in some embodiments, the shunting shaft 522 can be formed of stainless steel, platinum iridium, thermoplastic, PEEK, and the like. The distal portion 524 can be shape-set so that the distal portion 524 tends to self-bend into a curved shape when the distal portion 524 is unconstrained, such as when the distal portion 524 extends out from the side opening 515 of the catheter shaft 510. Prior to extension, the distal portion 524 may be maintained in a less curved shaped. In some embodiments, the catheter shaft 510 has a sufficiently resilient body to resist deformation due to the shape-set, self-bending property of the distal portion 524 of the shunting shaft 522.

As shown in FIG. 5B, the tissue-removal assembly 520 includes a cutting component 525 coupled to the distal portion 524 of the shunting shaft 522. The cutting component 525 has a ring shape, is disposed on an edge of the distal portion 524 and configured to cut and/or remove an area of tissue from a tissue wall (e.g., the vessel wall of a patient's CS). In some embodiments, the cutting component 525 can include an ablation electrode to deliver a radiofrequency (RF) ablation on the tissue in contact. In some embodiments, the cutting component 525 can include a mechanical cutting member, for example, a sharp cutting edge to cut the tissue in contact to the cutting component 525.

As shown in FIG. 5B, the tissue-removal assembly 520 further includes a puncture element 530 being extendable from the distal portion 524 of the shunting shaft 522. A puncture element shaft 532 movably connects the puncture element 530 to the distal portion 524 of the shunting shaft 522. The puncture element shaft 532 is configured to move the puncture element 530 between an extended state (e.g., FIG. 5B) and a retracted state (e.g., FIG. 5C). At the retracted state, the puncture element shaft 532 is at least partially received inside a lumen of the distal portion 524 of the shunting shaft 522. At the extended state, the puncture element shaft 532 extends out of the lumen of the shunting shaft 522 such that the puncture element 530 moves away from the cutting component 525.

As shown in FIG. 5B, the puncture element 530 further includes a puncture tip 534 at a distal point 531 of the puncture element 530. The puncture tip 534 can include an electrode to deliver a radiofrequency (RF) ablation or a mechanical puncturing tip. In some embodiments, the puncture element 530 has a curved cone shape with a second curvature. In some embodiments, the second curvature of the puncture element 530 can have the same sign of the first curvature of the distal portion 524 of the shunting shaft 522. For example, the distal portion 524 of the shunting shaft 522 may be curved to form a first angle $\theta_1$ with respect to the axis 510*a* of the catheter shaft 510, and the puncture element 530 may be further curved to form a second angle $\theta_2$ with respect to the axis 510*a* of the catheter shaft 510. The second angle $\theta_2$ can be greater than the first angle $\theta_1$.

As shown in FIG. 5B, the puncture element 530 further includes an array of tissue capturing structures 536 coupled to the puncture element 530. In some embodiments, the tissue capturing elements 536 can be part of the puncture element 530. For example, the puncture element 530 with the tissue capturing structures 536 can be formed by machining into a solid material body as a one-piece structure. In some embodiments, the puncture element 530 and the tissue capturing structures 536 can be formed separately and then coupled with each other by, e.g., welding or bonding.

Figure 6A:
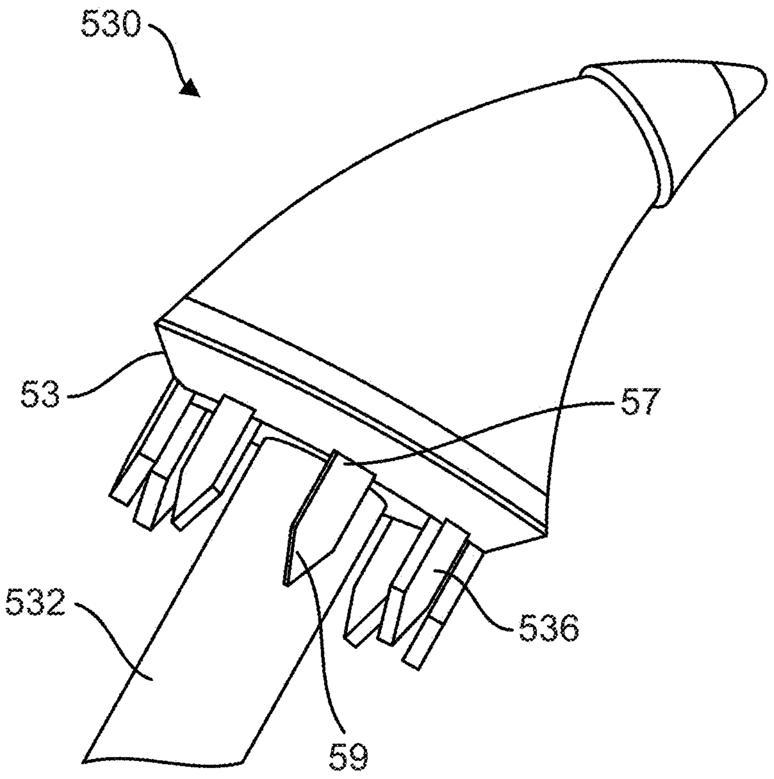
FIG. 6A is a side view of an example of a puncture element, in accordance with embodiments of the present disclosure.

FIG. 6A illustrates an enlarged side view of the puncture element 530 connecting to the puncture element shaft 532. The array of tissue capturing structures 536 is configured to capture an area of tissue from the tissue wall when the puncture element 530 is retracted from the extended state (FIG. 5B) to the retracted state (FIG. 5C). As shown in the embodiment depicted in FIG. 6A, each of tissue capturing structures 536 includes a first end 57 disposed on a surface of the puncture element 530 and a second end or tip 59 projecting from the puncture element 530 toward the distal portion 524 of the shunting shaft 522. In the embodiment depicted in FIG. 6A, the array of tissue capturing structures 536 is disposed on a rear surface 53 of the puncture element 530.

In some embodiments, the tissue-removal assembly 520 is deployed in the shaft lumen 514 of the catheter shaft 510 at a first state. For example, the shunting shaft 522 is received and advanced inside the shaft lumen 514 of the catheter shaft 510. The tissue-removal assembly 520 can be operated to a second state, where the distal portion 524 of the shunting shaft extends from the side opening 515 of the catheter shaft 510 to form a curved shape with a first curvature. When the puncture element 530 approaches the tissue wall 5, the puncture element shaft 532 can extend to move the puncture element 530 from the retracted state to the extended state to puncture through tissue wall 5, as illustrated in FIG. 5B. The puncture element shaft 532 can then be retracted such that the tissue capturing structures 536 grab an area of tissue 52 from the tissue wall 5, as shown in FIG. 5C. The rear surface 53 and/or the tissue capturing structures 536 can engage the cutting component 525 such that a periphery of the area of tissue 52 in contact to the cutting component 525 can be cut from the tissue wall 5, as shown in FIG. 5D. The area of tissue 52 cut from the tissue wall 5 can be received and collected inside the opening 526 of the shunting shaft 522 and removed along with the shunting shaft 522 when the shunting shaft 522 is retraced into the shaft lumen 514 of the catheter shaft 510. After the area of tissue 52 is removed from the tissue wall 5, an opening 52' is formed in the tissue wall 5.

Figure 6B:
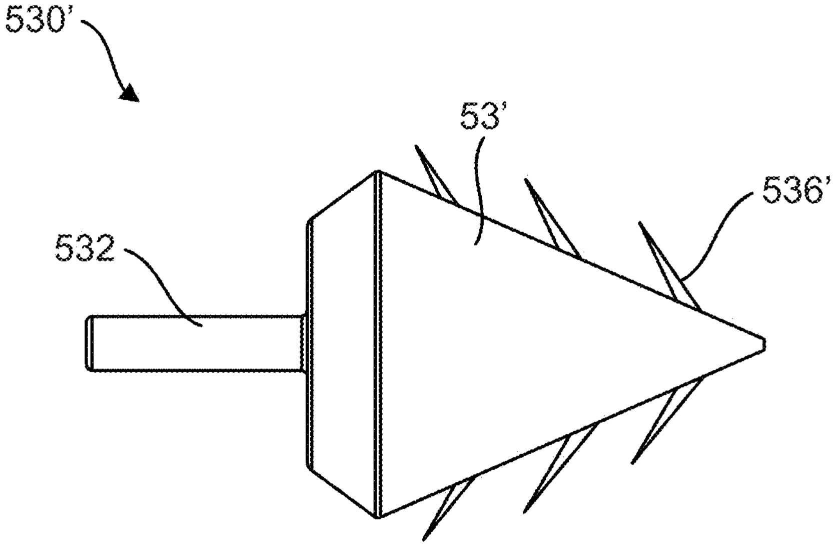
FIG. 6B is a side view of another example of a puncture element, in accordance with embodiments of the present disclosure.
Figure 7A:
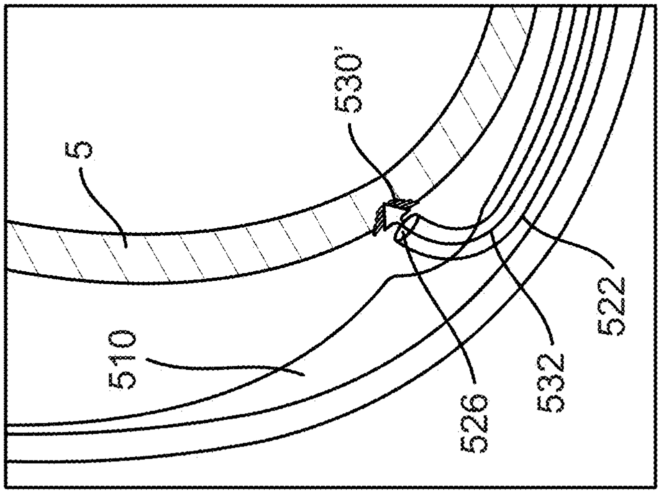
FIGS. 7A-7C are schematic diagrams of a tissue-removal assembly utilizing the puncture element of FIG. 6B to create a shunt in a tissue wall, in accordance with embodiments of the present disclosure.
Figure 7B:
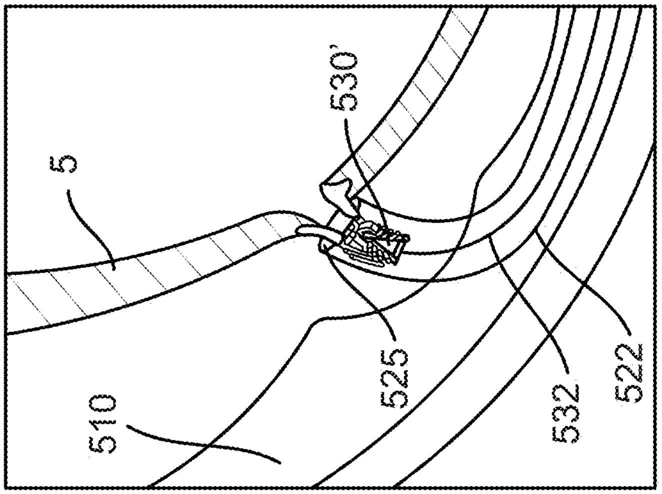
Figure 7C:
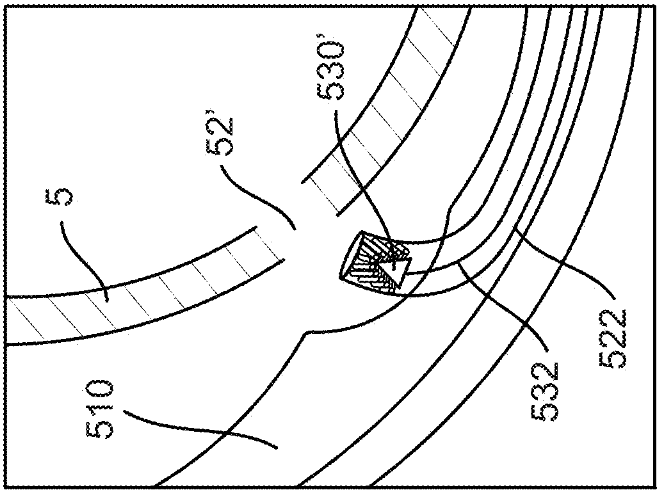

In some embodiments, a puncture element described herein can have various configurations to puncture a tissue wall when the shunting shaft is extended and to capture an area of tissue from the tissue wall when the shunting shaft is retracted. For example, in the embodiment depicted in FIG. 6B, the puncture element 530' has a cone shape and includes an array of tissue capturing structures 536' each being a sharp projection projecting from a conical surface 53' of the puncture element 530'toward the cutting component 525. The puncture element 530' can be completely received inside the opening 526 of the shunting shaft 522 (e.g., as illustrated in FIG. 7B). As shown in FIG. 7A, when the puncture element 530' approaches the tissue wall 5, the puncture element shaft 532 can extend to move the puncture element 530' out of the opening 526 to puncture through the tissue wall 5. The puncture element shaft 532 can then be retracted such that the tissue capturing structures 536' grab an area of tissue 52 from the tissue wall 5 into the opening 526 of the distal portion 524 of the area of tissue 52, as shown in FIG. 7B. The tissue capturing structures 536' can act as barbs to allow the tissue to stick onto the tissue capturing structures 536'. The tissue capturing structures 536' can then drag the tissue into the opening 526 such that the cutting component 525 can cut the area of tissue 52 from the tissue wall 5, as shown in FIG. 7B. In some embodiments, the cutting component 525 can include ablation electrode(s) to deliver ablative energy to cut/remove the area of tissue 52. The area of tissue 52 cut from the tissue wall 5 can be received inside the opening 526 of the shunting shaft 522 and be removed along the shunting shaft 522 when the shunting shaft 522 is retraced into the shaft lumen 514 of the catheter shaft 510. After the area of tissue 52 is removed from the tissue wall 5, an opening 52' is formed in the tissue wall 5, as shown in FIG. 7C.

Figure 8A:
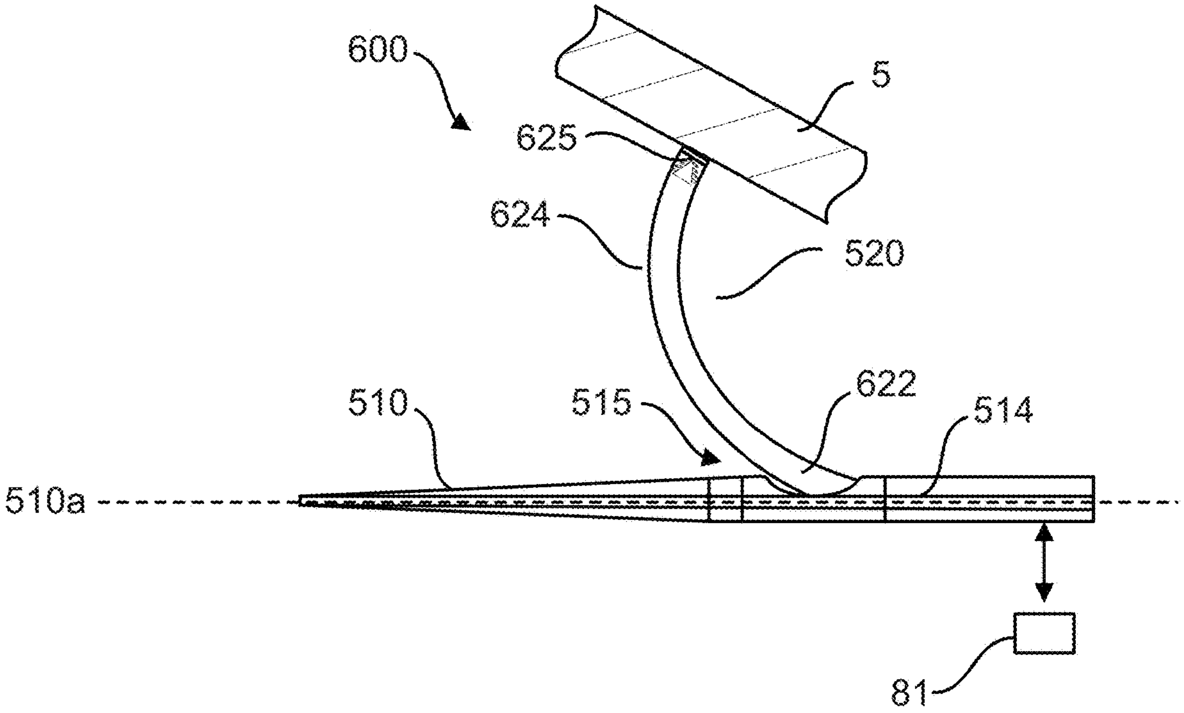
FIGS. 8A-8B are schematic diagrams illustrating an example of a tissue-removal assembly, in accordance with embodiments of the present disclosure.
Figure 8B:
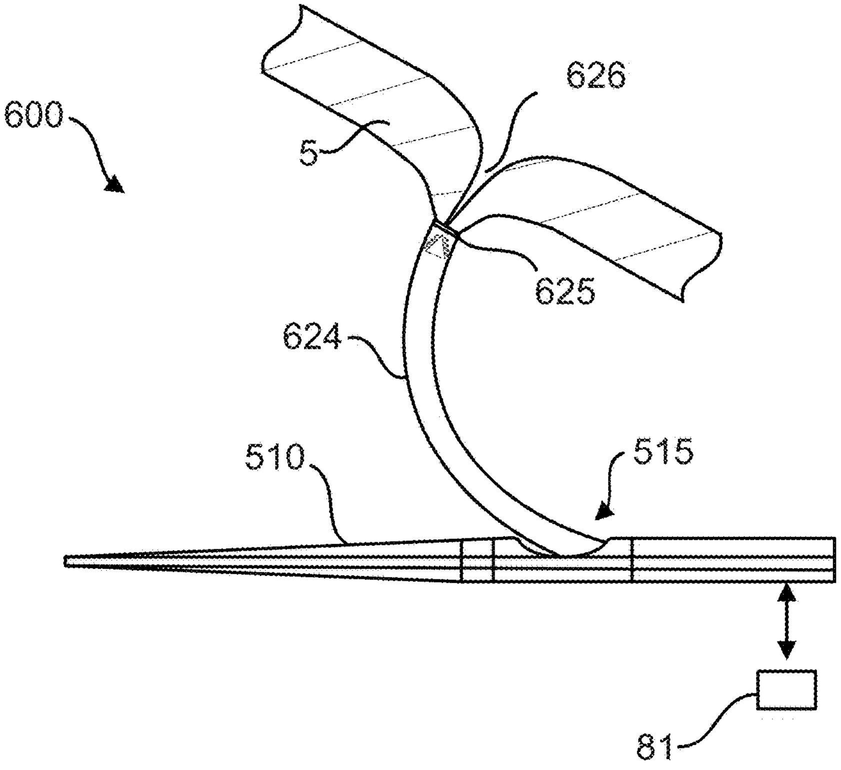
Figure 8C:
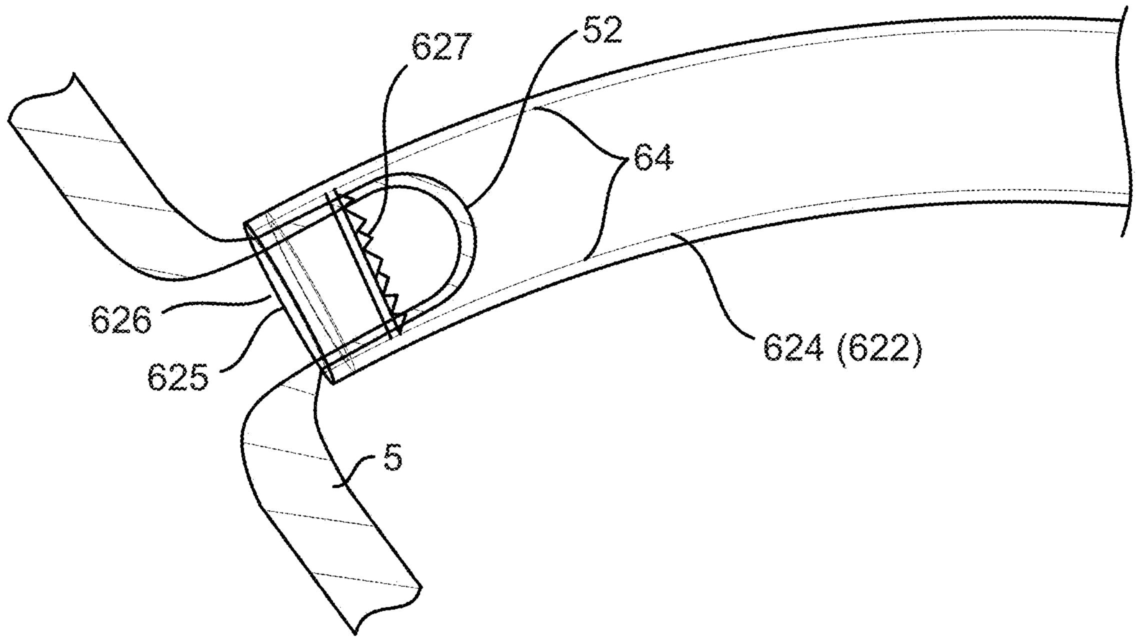
FIGS. 8C-8D are schematic diagrams illustrating a portion of the tissue-removal assembly of FIGS. 8A-8B, in accordance with embodiments of the present disclosure.
Figure 8D:
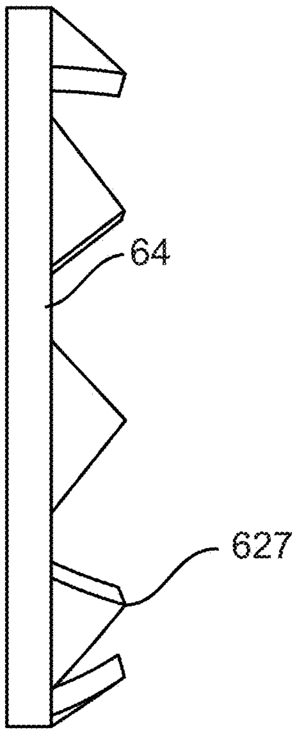

In some embodiments, a vacuum mechanism can fluidly connect to the distal portion of a shunting shaft to generate a reduced pressure at an opening of the distal portion of the shunting shaft. When the distal portion of the shunting shaft is deployed adjacent to or in contact to the issue wall, an area of tissue can be pulled by suction into the opening of the distal portion of the shunting shaft. As shown in the embodiment of FIGS. 8A and 8B, a shunting catheter 600 includes a tissue-removal assembly 620 including a shunting shaft 622 extends out of the side opening 515 of the catheter shaft 510. The shunting shaft 622 can have a lumen functionally connected to a vacuum mechanism 81 at a proximal end thereof (not shown). The vacuum mechanism 81 can include, for example, a vacuum pump, to generate a reduced pressure at the opening 626 of the distal portion 624 of the shunting shaft 622. When the shunting shaft 622 is deployed to extend out of the side opening 515 of the catheter shaft 510, the opening 626 approaches and contacts the tissue wall 5. The vacuum mechanism 81 can be turned on to pull by suction an area 52 of tissue into the opening 626, as shown in FIG. 8C. The distal portion 624 of the shunting shaft 622 includes a retention feature 627 (e.g., as illustrated in FIGS. 8C and 8D) disposed on a wall 64 (e.g., an inner surface thereof). In some embodiments, a cutting member 625 can be provided at the opening 626, adjacent to the retention feature 627. In some embodiments, the retention feature 627 is configured to retain the area of tissue 52 inside the opening 626. With the tissue 52 being retained in position, the cutting member 625 at the opening 626 can then cut and remove the area of tissue 52 from the tissue wall 5 to create an opening in the tissue wall 5. The cutting component 625 can include ablation electrode(s) to deliver ablative energy. In some embodiments, the retention feature 627 can include an array of spikes arranged on the inner wall 64 of the shunting shaft 622, as shown in FIG. 8D.

Figure 9A:
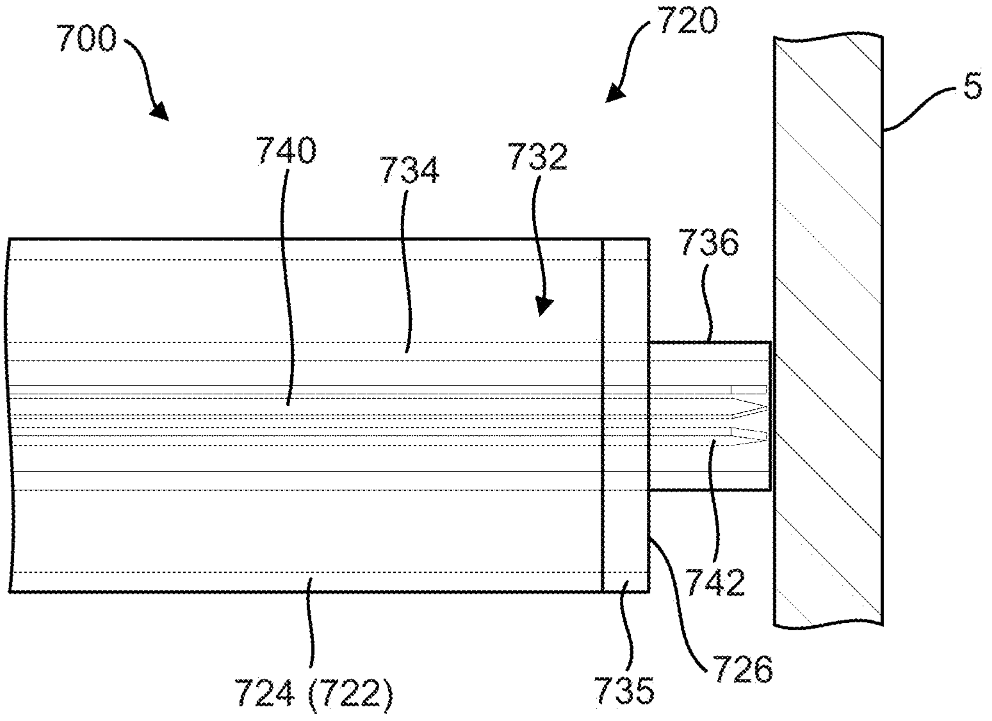
FIGS. 9A-9D are schematic diagrams of an example of a tissue-removal assembly utilizing a puncture element to create a shunt in a tissue wall, in accordance with embodiments of the present disclosure.
Figure 9B:
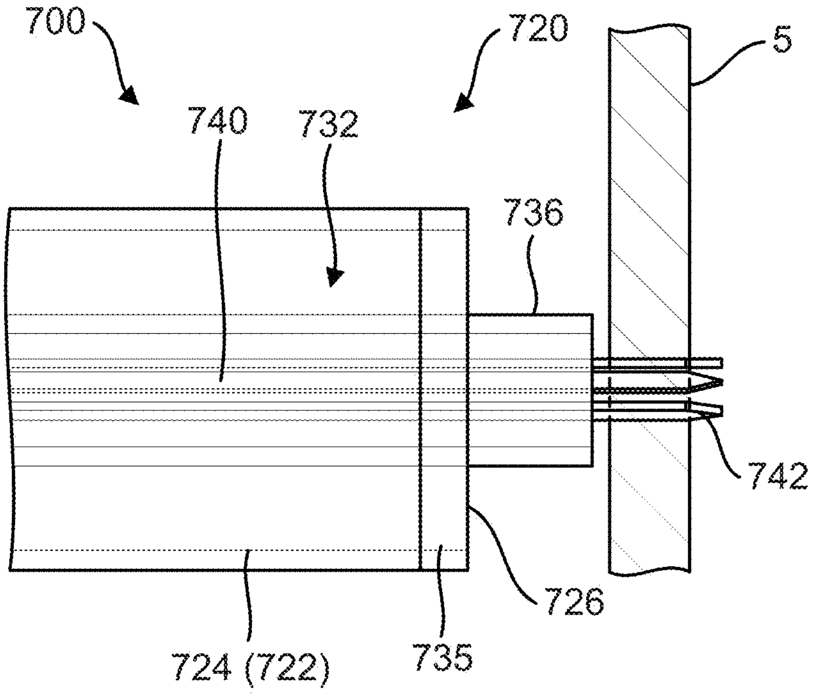
Figure 9C:
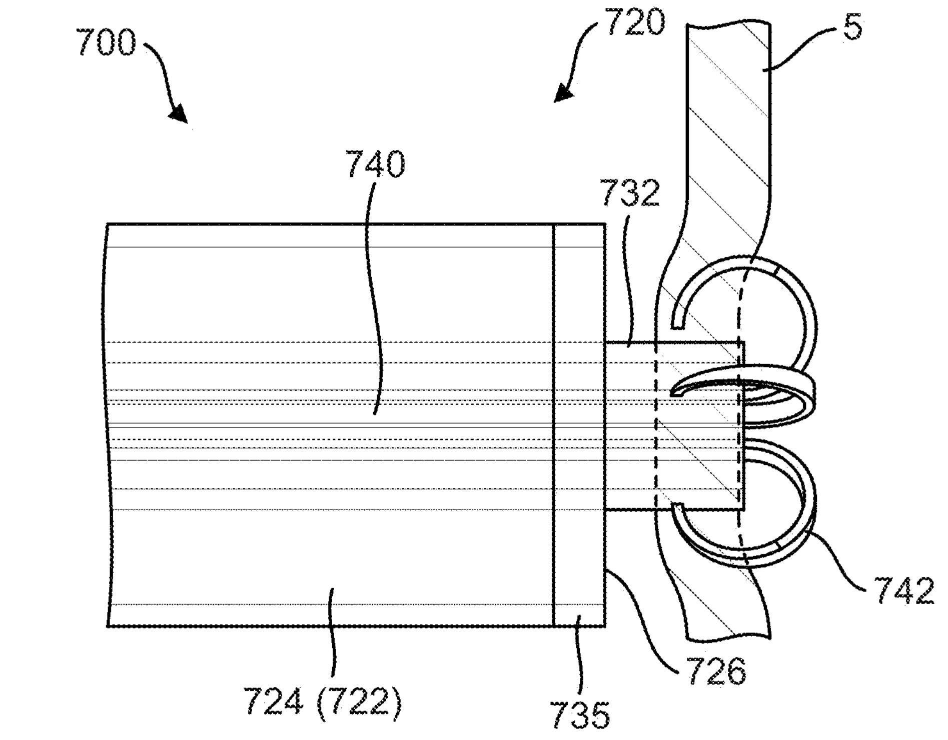
Figure 9D:
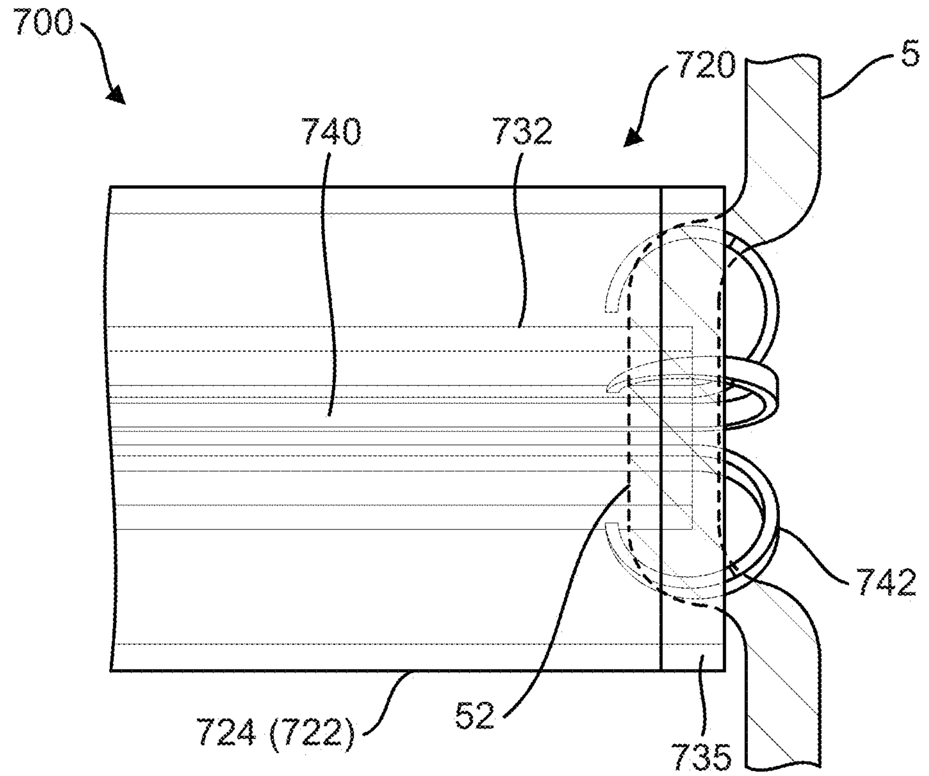

FIGS. 9A-9D are schematic diagrams illustrating an example of a shunting catheter 700 including a tissue-removal assembly 720, in accordance with some embodiments of the present disclosure. The tissue-removal assembly 720 includes a puncture element shaft 732 which is received inside a lumen of a distal portion 724 of a shunting shaft 722. The puncture element shaft 732 includes a sheath 734 and an elongate punching member 740 received inside the sheath 734. The puncture element shaft 732 includes a distal end 736 being extendable out of an opening 726 of the shunting shaft 722. When the distal end 736 of the puncture element shaft 732 approaches to contact with or in close proximity to the tissue wall 5, the elongate punching member 740 can be extended such that the distal portion 742 of the elongate punching member 740 can punch through the tissue wall 5 (FIG. 9B). The sheath 734 can then be retracted to expose the distal portion 742 of the elongate punching member 740 out of the sheath 734 such that each of the distal portion 742 of the elongate punching member 740 can bend to form a hook shape (FIG. 9C). In some embodiments, the distal portion 742 can include multiple nitinol wires or other shape-set configurations (e.g., a laser cut hypotube or LCHT), which can act as anchors to grab and retain an area of tissue 52. The puncture element shaft 732 can then be retracted to grab the area of tissue 52 into the opening 726 of the shunting shaft 722. A cutting member 725 at the opening 726 can then cut the area of tissue 52 from the tissue wall 5, as shown in FIG. 9D. In some embodiments, the cutting component 725 and/or the distal portion 742 can include ablation electrode(s) to deliver ablative energy to facilitate the cutting of the tissue 52 from the tissue wall 5.

Figure 10A:
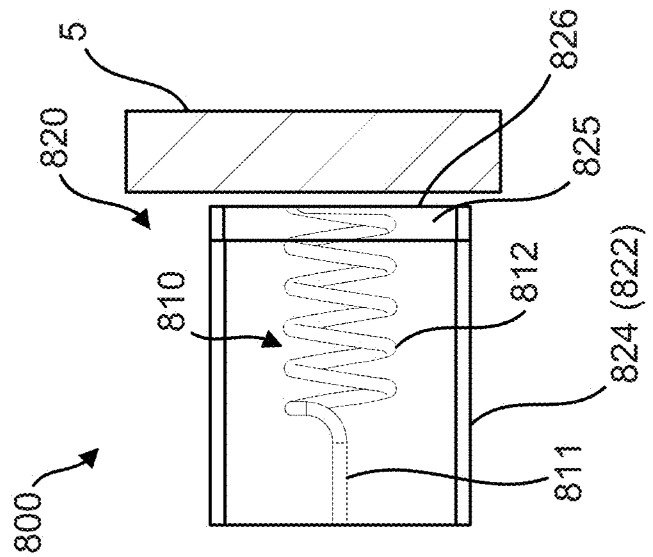
FIGS. 10A-10C are schematic diagrams of side views of an example of a tissue-removal assembly including a helical anchor, in accordance with embodiments of the present disclosure.
Figure 10B:
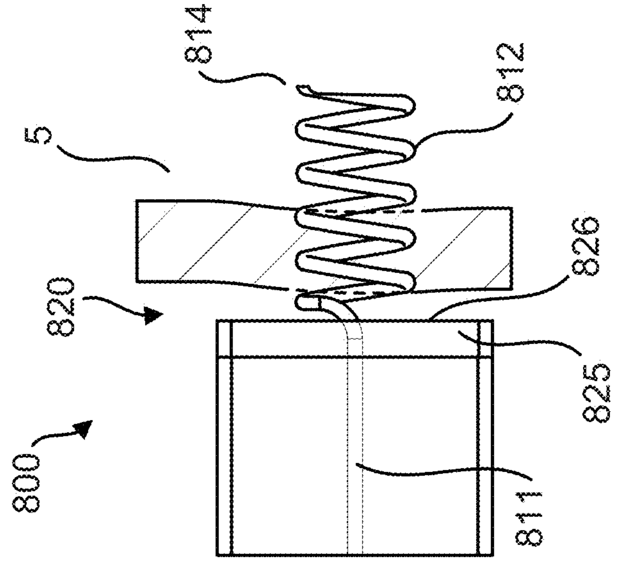
Figure 10C:
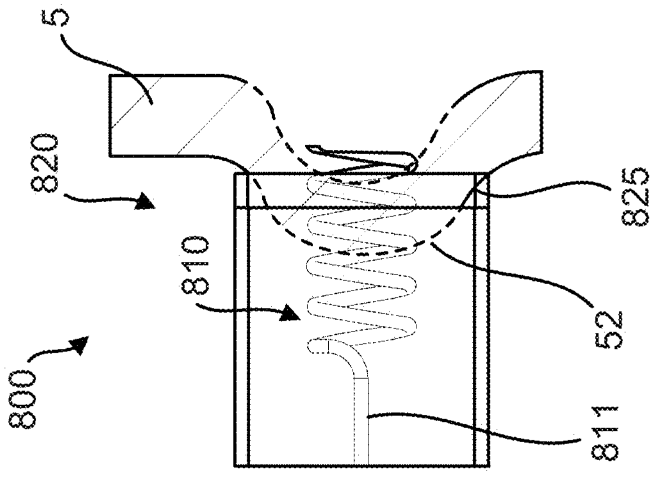
Figure 11A:
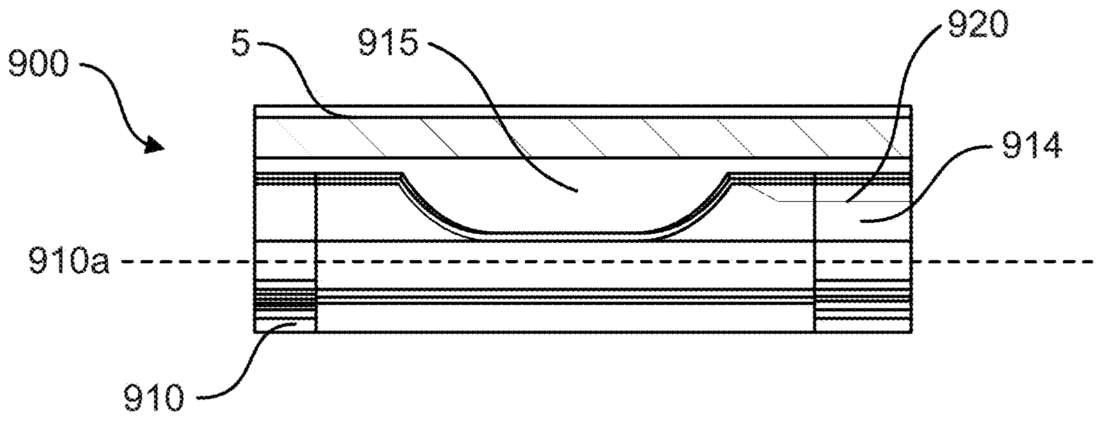
FIGS. 11A-11D are schematic diagrams of side views of an example of a shunting catheter, in accordance with embodiments of the present disclosure.
Figure 11B:
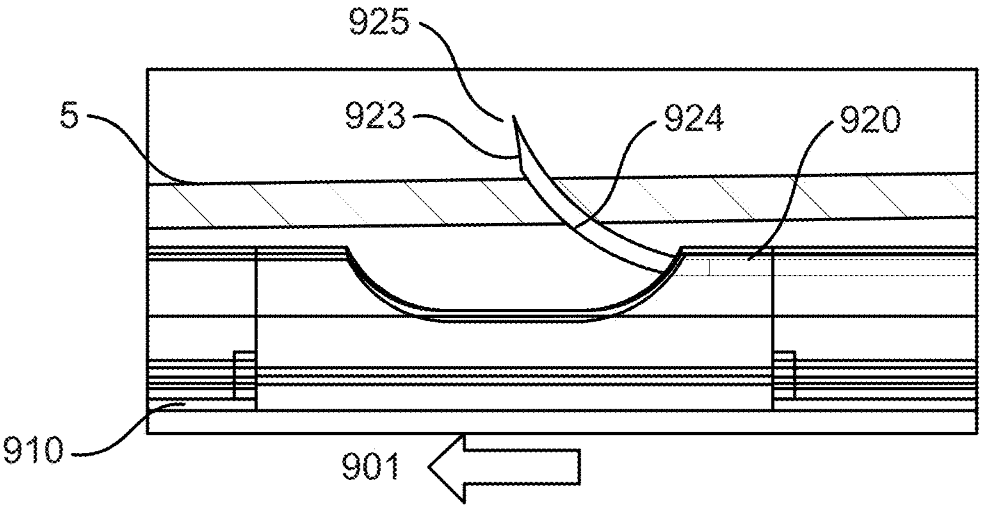
Figure 11C:
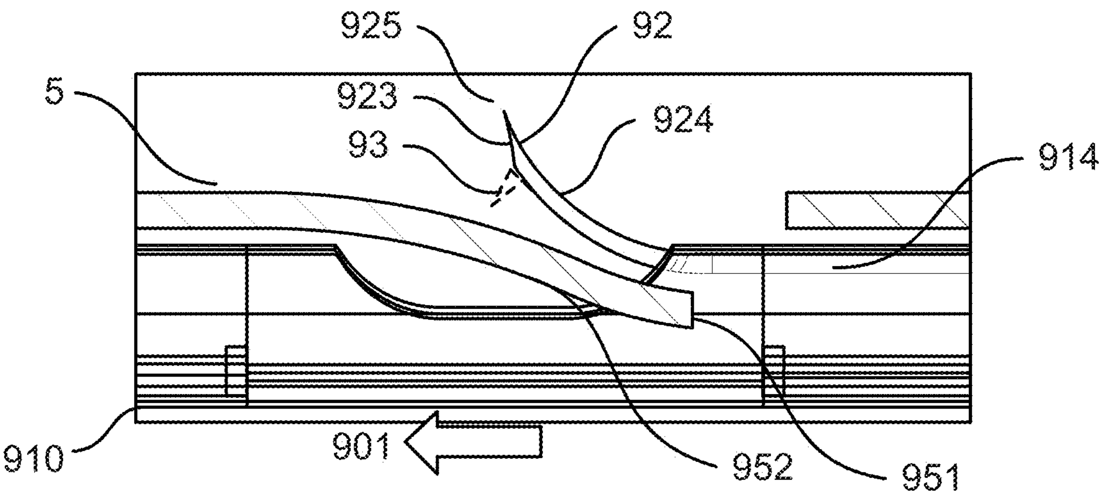
Figure 11D:
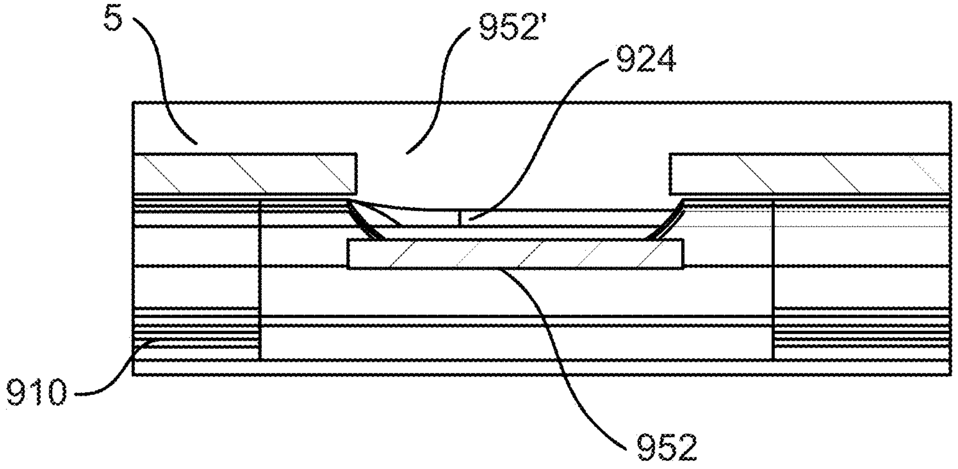

FIGS. 10A-10C are schematic diagrams of an example of a tissue-removal assembly 820 utilizing a puncture element to create a shunt in a tissue wall, in accordance with embodiments of the present disclosure. As shown, a shunting catheter 800 includes the tissue-removal assembly 820. The tissue-removal assembly 820 includes a helical anchor 810 being extendable from an opening 826 of the distal portion 824 of the shunting shaft 822. The helical anchor 810 includes a helical portion 812, a shaft 811 to support and rotate the helical portion 812, and a tip 814 to puncture through the tissue wall 5. When the distal portion 824 approaches the tissue wall 5 to contact with or be in close proximity to the tissue wall 5, the shaft 811 can be extended/rotated/twisted by an anchor driver connected to a remote end (not shown) of the shaft 811 such that the helical portion 812 can screw into and punch through the tissue wall 5 (FIG. 10B). The shaft 811 can then be retracted to grab the area of tissue 52 into the opening 826 of the shunting shaft 822. A cutting member 825 at the opening 826 can then cut the area of tissue 52 from the tissue wall 5, as shown in FIG. 10C.

FIGS. 11A-11D are schematic diagrams of side views of an example of a shunting catheter 900, in accordance with embodiments of the present disclosure. In some embodiments, the shunting catheter 900 includes a catheter shaft 910 extending along an axis 910*a*. The catheter shaft 910 includes a shaft lumen 914 and a side opening 915 in communication with the shaft lumen 914. A shunting shaft 920 has a distal portion 924 being extendable from the side opening 915 of the catheter shaft 910. In some embodiments, the shunting shaft 920 can be formed of a laser cut hypotube (LCHT). For example, the shunting catheter 900 is first deployed to have the catheter shaft 910 to be substantially parallel to the tissue wall 5 and to have the side opening 915 to face the area of tissue 952 to be removed from the tissue wall 5 (e.g., FIG. 11A or FIG. 11D).

In some embodiments, the distal portion 924 of the shunting shaft 920 received inside the shaft lumen 914 can then extend out of the side opening 915. The distal portion 924 includes a shovel structure 92 having one or more cutting blades 923 and a cutting edge 925 to cut through the tissue wall 5 (e.g., FIGS. 11B and 11C). The catheter shaft 910 can be moved along the direction 901 such that an end 951 of the cut tissue is directed into the shaft lumen 914 of the catheter shaft 910 (e.g., FIG. 11C). The shunting shaft 920 can then be pulled back, e.g., by a guidewire or pull wire, to have the shovel structure to cut an area 952 of tissue from the tissue wall. In some embodiments, the shovel structure can include a slicing member 93 extending from a base of the shovel structure to cut the area 952 from the tissue wall 5 (e.g., FIG. 11C). In some embodiments, the area 952 of tissue and the shunt 952' can have a substantially oval shape instead of a circular shape.

Figure 12:
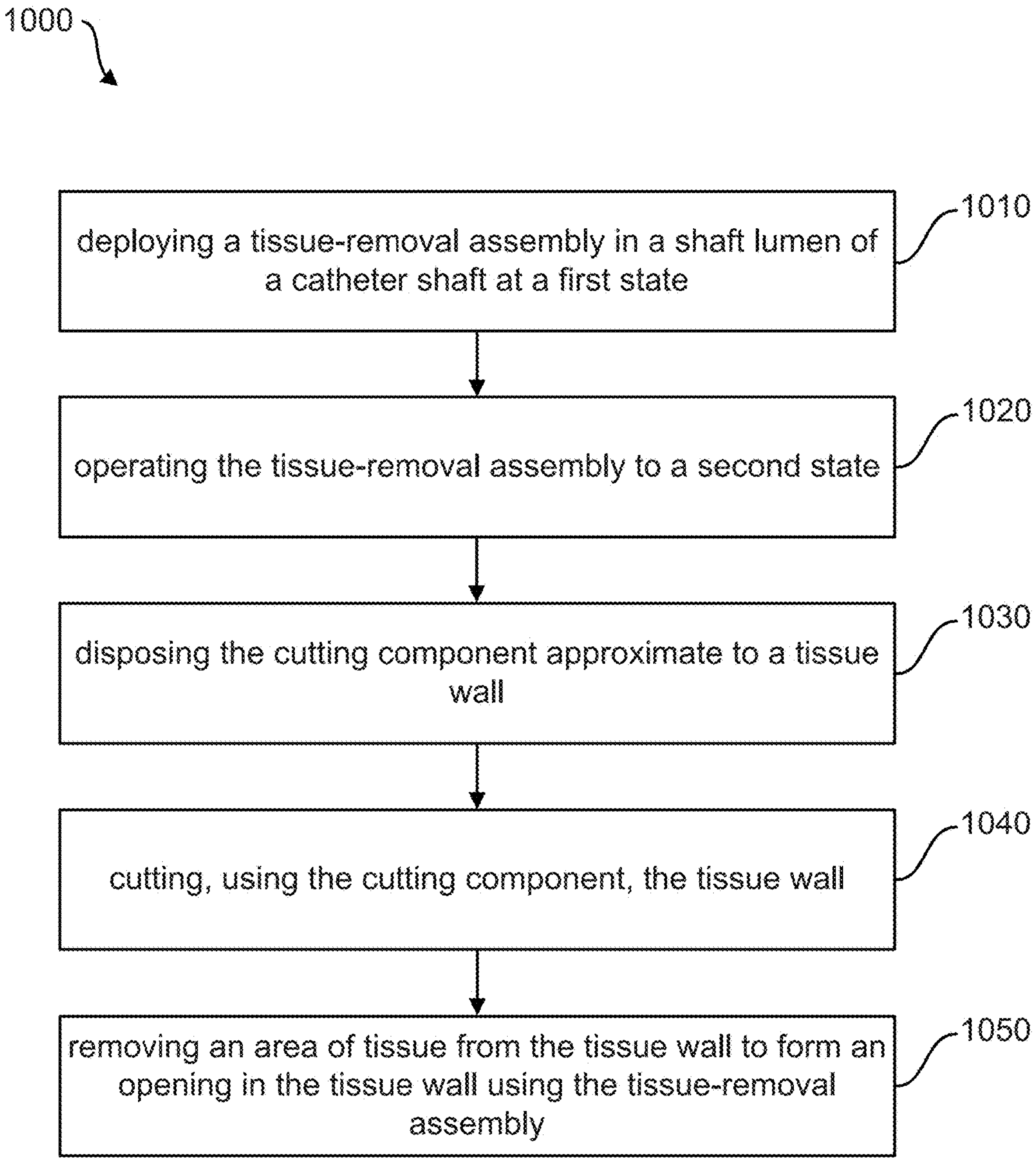
FIG. 12 is a flow diagram illustrating an example process of creating a shunt in a patient, in accordance with embodiments of the present disclosure.

FIG. 12 is a flow diagram illustrating an example method 1000 of creating a shunt in a patient, in accordance with embodiments of the present disclosure. The method is described in relation to the catheters discussed previously here, however, any suitable electroporation catheter can be used in the method. Aspects of embodiments of the method may be performed, for example, by a shunting catheter system or a controller (e.g., the system 104 in FIG. 1, the controller 112 in FIG. 1). One or more steps of method are optional and/or can be modified by one or more steps of other embodiments described herein. Additionally, one or more steps of other embodiments described herein may be added to the method. In some embodiments, the shunt may be formed in a coronary sinus of a patient. In certain embodiments, the shunt includes an opening between a patient's coronary sinus and left atrium.

According to certain embodiments, the method 1000 includes the process 1010 of deploying a tissue-removal assembly in a shaft lumen of a catheter shaft at a first state. The tissue-removal assembly includes a shunting shaft and a cutting component disposed at a distal end of the shunting shaft. In some embodiments, the cutting component includes an ablation electrode, and the cutting the tissue wall includes delivering ablation energy to a target location using the ablation electrode. In some embodiments, the cutting component includes a shovel structure extending from the distal end of the shunting shaft. In some embodiments, the cutting component further includes a slicing member extending from a base of the shovel structure.

According to some embodiments, the method 1000 includes the process 1020 of operating the tissue-removal assembly to a second state. The distal end of the shunting shaft extends from a side opening of the catheter shaft with a curved shape.

In some embodiments, the method 1000 further includes extending a puncture element from the distal end of the shunting shaft. In certain examples, a puncture element shaft movably connects the puncture element to the distal end of the shunting shaft, and is configured to move the puncture element between an extended state and a retracted state.

In some embodiments, the method 1000 further includes moving the puncture element to the extended state to puncture through the tissue wall. The puncture element further includes a puncturing tip at a distal portion thereof.

In some embodiments, the puncture element shaft includes a sheath and a plurality of shape-memory wires received in the sheath. When the puncture element is at the extended state, the method 1000 further includes retracting the sheath to expose a distal portion of the plurality of shape-memory wires to form a plurality of anchors.

In some embodiments, the method 1000 further includes extending a plurality of puncturing wires from the distal end of the shunting shaft to puncture through the tissue wall, forming a plurality of anchors at a distal portion of the plurality of puncturing wires, and retracting the plurality of anchors to grab the area of tissue into the distal end of the shunting shaft.

In some embodiments, the method 1000 further includes extending a helical anchor from the distal end of the shunting shaft to puncture through the area of tissue and retracting the helical anchor to grab the area of tissue into the distal end of the shunting shaft.

In some embodiments, the method 1000 further includes expanding the distal end of the shunting shaft to form a basket structure.

According to certain embodiments, the method 1000 includes the process 1030 of disposing the cutting component approximate to a tissue wall of a patient. In some embodiments, the method 1000 further includes retracting the puncture element back to the retracted state. The puncture element further includes an array of tissue capturing structures to grab the area of tissue into the distal end of the shunting shaft. In some embodiments, the method 1000 further includes grabbing the area of tissue into the distal end of the shunting shaft using the plurality of anchors when the puncture element is moved to the retracted state.

In some embodiments, the method 1000 further includes generating a reduced pressure at the distal end of the shunting shaft to pull the area of tissue into the distal end of the shunting shaft.

According to certain embodiments, the method 1000 includes the process 1040 of cutting, using the cutting component, the tissue wall.

According to some embodiments, the method 1000 includes the process 1050 of removing an area of tissue from the tissue wall to form a shunt (e.g., an opening, one or more openings) in the tissue wall using the tissue-removal assembly.

In some embodiments, a hybrid process can be applied to create a shunt on a cardiovascular system wall in a patient. For example, a relatively small portion/area of tissue (e.g., having an outer diameter or width from 1 mm to 7 mm) can be removed from a tissue wall to create a first opening, using the shunting catheters and methods described herein. The first opening can have a first dimension (e.g., an outer diameter or width/length) from 1 mm to 7 mm. Expansion mechanisms can then be applied to expand the first opening to a second opening having a second dimension greater than the first dimension. The second dimension (e.g., an outer diameter or width/length) can be in the range from 3 mm to 15 mm. Example expansion mechanisms can include a balloon, a Niti frame, or other suitable expandable elements. For example, FIG. 3 illustrates the expandable element 312 which may be a balloon, or a basket configured to expand the first opening to a target diameter. In some embodiments, after the first opening is created, an inner catheter including a tissue-removal assembly can be exchanged with another catheter including the expansion mechanism which can be deployed to expand the first opening to the target diameter.

According to some embodiments of the present disclosure, a shunting catheter includes a catheter shaft including a shaft lumen and a side opening, and a tissue-removal assembly disposed in the shaft lumen in a first state and including a shunting shaft being extendable from the side opening of the catheter shaft. The shunting shaft has a curved shape when extending from the side opening to a second state, and the shunting shaft has an opening at a distal end thereof. The tissue-removal assembly includes a cutting component disposed at the distal end of the shunting shaft.

In certain embodiments, the cutting component includes an ablation electrode or a mechanical cutting member.

In certain embodiments, the cutting component has a ring shape.

In certain embodiments, the tissue-removal assembly further includes a puncture element being extendable from the distal end of the shunting shaft, and a puncture element shaft movably connecting the puncture element to the distal end of the shunting shaft. The puncture element shaft is configured to move the puncture element between an extended state and a retracted state.

In certain embodiments, the puncture element further includes a puncturing tip at a distal portion thereof.

In certain embodiments, the puncturing tip includes an electrode to deliver a radiofrequency (RF) ablation or a mechanical puncturing tip.

In certain embodiments, the puncture element has a curved cone shape.

In certain embodiments, the puncture element further includes an array of tissue capturing structures, each tissue capturing structure of the array of tissue capturing structures having a first end disposed at a surface of the puncture element and a second end extended from the surface of the puncture element.

In certain embodiments, the puncture element shaft includes a sheath and an elongate puncturing member received in the sheath, and the elongate puncturing member is extendable from the sheath to form an anchor.

In certain embodiments, the puncture element is a curved puncture element including a curved body and a tip, the tip of the curved puncture element extending along a first axis and the curved body extending along a second axis, wherein the first axis and the second axis form an angle greater than zero degrees.

In certain embodiments, the tissue-removal assembly includes a plurality of puncturing wires extendable from the distal end of the shunting shaft, a distal portion of the plurality of puncturing wires being configured to form a plurality of anchors.

In certain embodiments, the tissue-removal assembly includes a helical anchor being extendable from the distal end of the shunting shaft.

In certain embodiments, the distal end of the shunting shaft further includes an expandable basket structure adjacent to the cutting component.

In certain embodiments, the cutting component includes a shovel structure extending from the distal end of the shunting shaft.

In certain embodiments, the cutting component further includes a slicing member extending from a base of the shovel structure.

In certain embodiments, the shunting catheter further includes a vacuum mechanism fluidly connected to the opening at the distal end of the shunting shaft to generate a reduced pressure at the opening.

In certain embodiments, the distal end of the shunting shaft includes a retention feature disposed on an inner wall of the distal end adjacent to the cutting component.

According to certain embodiments of the present disclosure, a method of creating a shunt includes deploying a tissue-removal assembly in a shaft lumen of a catheter shaft at a first state, the tissue-removal assembly including a shunting shaft and a cutting component disposed at a distal end of the shunting shaft, operating the tissue-removal assembly to a second state, wherein the distal end of the shunting shaft extends from a side opening of the catheter shaft with a curved shape, disposing the cutting component approximate to a tissue wall of a patient, cutting, using the cutting component, the tissue wall, and removing an area of tissue from the tissue wall to form an opening in the tissue wall using the tissue-removal assembly.

In certain embodiments, the cutting component includes an ablation electrode, and the cutting of the tissue wall includes delivering ablation energy to a target location using the ablation electrode.

In certain embodiments, the method further includes extending a puncture element from the distal end of the shunting shaft. A puncture element shaft movably connects the puncture element to the distal end of the shunting shaft and is configured to move the puncture element between an extended state and a retracted state.

In certain embodiments, the method further includes moving the puncture element to the extended state to puncture through the tissue wall. The puncture element further includes a puncturing tip at a distal portion thereof.

In certain embodiments, the method further includes retracting the puncture element back to the retracted state. The puncture element further includes an array of tissue capturing structures to grab the area of tissue into an opening at the distal end of the shunting shaft.

In certain embodiments, the puncture element shaft includes a sheath and an elongate puncturing member received in the sheath, and when the puncture element is at the extended state, exposing a distal portion of the elongate puncturing member to form an anchor.

In certain embodiments, the method further includes grabbing the area of tissue into an opening at the distal end of the shunting shaft using the anchor when the puncture element is moved to the retracted state.

In certain embodiments, the method further includes extending an elongate puncturing member from the distal end of the shunting shaft to puncture through the tissue wall, forming an anchor at a distal portion of the elongate puncturing member, and retracting the anchor to grab the area of tissue into an opening at the distal end of the shunting shaft.

In certain embodiments, the method further includes extending a helical anchor from the distal end of the shunting shaft to puncture through the area of tissue and retracting the helical anchor to grab the area of tissue into an opening at the distal end of the shunting shaft.

In certain embodiments, the method further includes expanding the distal end of the shunting shaft to form a basket structure adjacent to the cutting component.

In certain embodiments, the cutting component includes a shovel structure extending from the distal end of the shunting shaft.

In certain embodiments, the cutting component further includes a slicing component extending from a base of the shovel structure.

In certain embodiments, the method further includes generating a reduced pressure at an opening at the distal end of the shunting shaft to pull the area of tissue into the opening.

Various modifications and additions can be made to the exemplary embodiments discussed without departing from the scope of the present disclosure. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A shunting catheter, comprising:

a catheter shaft including a shaft lumen and a side opening; and a tissue-removal assembly disposed in the shaft lumen in a first state and comprising a shunting shaft being extendable from the side opening of the catheter shaft, the shunting shaft having a curved shape when extending from the side opening to a second state, the shunting shaft having an opening at a distal end thereof;

wherein the shunting shaft comprises a cutting component disposed at the distal end of the shunting shaft;

wherein the cutting component extends along a circumferential direction of the opening at the distal end of the shunting shaft, wherein the tissue-removal assembly further comprises:

a puncture element being extendable from the distal end of the shunting shaft; and a puncture element shaft connecting the puncture element to the distal end of the shunting shaft, the puncture element shaft configured to mechanically support the puncture element when the puncture element is extended from the shunting shaft at an extended state; and wherein:

the puncture element includes a rear surface that is coupled to the puncture element shaft;

the rear surface of the puncture element has a first diameter;

the puncture element shaft has a second diameter; and the first diameter is greater than the second diameter.

2. The shunting catheter of claim 1, wherein the cutting component comprises an ablation electrode or a mechanical cutting member.

3. The shunting catheter of claim 1, wherein the cutting component has a ring shape.

4. The shunting catheter of claim 1, wherein:

the puncture element shaft is configured to extend the puncture element at a first distance at the extended state and at a second distance at a retracted state, wherein the first distance is greater than the second distance.

5. The shunting catheter of claim 1, wherein the puncture element further comprises a puncturing tip at a distal portion, wherein the puncturing tip includes an electrode to deliver a radiofrequency (RF) ablation or a mechanical puncturing tip.

6. The shunting catheter of claim 1, wherein the puncture element has a curved cone shape.

7. The shunting catheter of claim 1, wherein the puncture element further comprises an array of tissue capturing structures, each tissue capturing structure of the array of tissue capturing structures having a first end disposed at a surface of the puncture element and a second end extended from the surface of the puncture element.

8. The shunting catheter of claim 1, wherein the puncture element shaft comprises a sheath and an elongate puncturing member received in the sheath, and the elongate puncturing member is extendable from the sheath to form an anchor.

9. The shunting catheter of claim 1, wherein the puncture element is a curved puncture element including a curved body and a tip, the tip of the curved puncture element extending along a first axis and the curved body extending along a second axis, wherein the first axis and the second axis form an angle greater than zero degrees.

10. The shunting catheter of claim 1, wherein the tissue-removal assembly comprises a plurality of puncturing wires extendable from the distal end of the shunting shaft, a distal portion of the plurality of puncturing wires being configured to form a plurality of anchors.

11. The shunting catheter of claim 1, wherein the tissue-removal assembly comprises a helical anchor being extendable from the distal end of the shunting shaft.

12. The shunting catheter of claim 1, wherein the distal end of the shunting shaft further comprises an expandable basket structure adjacent to the cutting component.

13. The shunting catheter of claim 1, wherein the cutting component comprises a shovel structure extending from the distal end of the shunting shaft.

14. The shunting catheter of claim 13, wherein the cutting component further comprises a slicing member extending from a base of the shovel structure.

15. The shunting catheter of claim 1, further comprising a vacuum mechanism fluidly connected to the opening at the distal end of the shunting shaft to generate a reduced pressure at the opening.

16. The shunting catheter of claim 1, wherein the distal end of the shunting shaft comprises a retention feature disposed on an inner wall of the distal end adjacent to the cutting component.

17. The shunting catheter of claim 1, wherein:

the tissue-removal assembly is configured to remove an area of tissue from the tissue wall to create a shunt at the second state; and the shunting shaft is configured to receive at least a portion of the removed area of tissue at a third state.

18. The shunting catheter of claim 17, wherein the shunt has an outer diameter in a range from 3 mm to 15 mm.

19. A method of creating a shunt, comprising:

deploying a tissue-removal assembly in a shaft lumen of a catheter shaft at a first state, the tissue-removal assembly comprising a shunting shaft having an opening at a distal end thereof, and the shunting shaft comprising a cutting component disposed at a distal end of the shunting shaft, the cutting component extending along a circumferential direction of the opening at the distal end of the shunting shaft;

operating the tissue-removal assembly to a second state, wherein the distal end of the shunting shaft extends from a side opening of the catheter shaft with a curved shape;

disposing the cutting component approximate to a tissue wall of a patient;

extending a puncture element from the distal end of the shunting shaft;

cutting, using the cutting component, the tissue wall; and removing an area of tissue from the tissue wall to form an opening in the tissue wall using the tissue-removal assembly, wherein a puncture element shaft connects the puncture element to the distal end of the shunting shaft, the puncture element shaft is configured to mechanically support the puncture element when the puncture element is extended from the shunting shaft at an extended state; and wherein:

the puncture element includes a rear surface that is coupled to the puncture element shaft;

the rear surface of the puncture element has a first diameter;

the puncture element shaft has a second diameter; and the first diameter is greater than the second diameter.

20. The method of claim 19, wherein the cutting component comprises an ablation electrode, and the cutting of the tissue wall comprises delivering ablation energy to a target location using the ablation electrode.

21. The method of claim 19, wherein the puncture element shaft is configured to extend the puncture element at a first distance at the extended state and at a second distance at a retracted state, wherein the first distance is greater than the second distance.

22. The method of claim 19, further comprising:

moving the puncture element to the extended state to puncture through the tissue wall, wherein the puncture element further comprises a puncturing tip at a distal portion thereof.

23. The method of claim 19, further comprising:

retracting the puncture element back to the retracted state, wherein the puncture element further comprises an array of tissue capturing structures to grab the area of tissue into an opening at the distal end of the shunting shaft.

24. The method of claim 19, wherein the puncture element shaft comprises a sheath and an elongate puncturing member received in the sheath, and when the puncture element is at the extended state, exposing a distal portion of the elongate puncturing member to form an anchor.

25. The method of claim 24, further comprising grabbing the area of tissue into an opening at the distal end of the shunting shaft using the anchor when the puncture element is moved to the retracted state.

26. The method of claim 19, further comprising:

extending an elongate puncturing member from the distal end of the shunting shaft to puncture through the tissue wall;

forming an anchor at a distal portion of the elongate puncturing member; and retracting the anchor to grab the area of tissue into an opening at the distal end of the shunting shaft.

27. The method of claim 19, further comprising:

extending a helical anchor from the distal end of the shunting shaft to puncture through the area of tissue; and retracting the helical anchor to grab the area of tissue into an opening at the distal end of the shunting shaft.

28. The method of claim 19, further comprising expanding the distal end of the shunting shaft to form a basket structure adjacent to the cutting component.

29. The method of claim 19, wherein the cutting component comprises a shovel structure extending from the distal end of the shunting shaft.

30. The method of claim 29, wherein the cutting component further comprises a slicing component extending from a base of the shovel structure.

31. The method of claim 19, further comprising generating a reduced pressure at an opening at the distal end of the shunting shaft to pull the area of tissue into the opening.

* * * * *